United States Patent
Franklin et al.

(10) Patent No.: US 11,525,124 B2
(45) Date of Patent: *Dec. 13, 2022

(54) PURIFICATION OF POLYMERASE COMPLEXES

(71) Applicant: ROCHE SEQUENCING SOLUTIONS, INC., Pleasanton, CA (US)

(72) Inventors: Helen Franklin, San Jose, CA (US); Cynthia Cech, Pleasanton, CA (US); Timothy Kellogg Craig, Campbell, CA (US); Aruna Ayer, Santa Clara, CA (US); Kirti Dhiman, Mountain View, CA (US); Natalie B. Chechelski Johnston, Redwood City, CA (US); Joshua N. Mabry, Woodside, CA (US); Arkadiusz Bibillo, Cupertino, CA (US); Peter Crisalli, Mountain View, CA (US); Randall W. Davis, Santa Clara, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 290 days.

This patent is subject to a terminal disclaimer.

(21) Appl. No.: 16/871,732

(22) Filed: May 11, 2020

(65) Prior Publication Data

US 2020/0277581 A1 Sep. 3, 2020

Related U.S. Application Data

(60) Division of application No. 15/989,109, filed on May 24, 2018, which is a continuation of application No. PCT/EP2016/078781, filed on Nov. 25, 2016.

(60) Provisional application No. 62/373,973, filed on Aug. 11, 2016, provisional application No. 62/295,010, filed on Feb. 13, 2016, provisional application No. 62/260,194, filed on Nov. 25, 2015.

(51) Int. Cl.
| | |
|---|---|
| C12N 9/12 | (2006.01) |
| C12Q 1/6869 | (2018.01) |
| B01L 9/00 | (2006.01) |
| C12N 9/96 | (2006.01) |
| C12Q 1/6806 | (2018.01) |
| C12Q 1/6874 | (2018.01) |

(52) U.S. Cl.
CPC ......... C12N 9/1252 (2013.01); C12Q 1/6869 (2013.01); *B01L 9/527* (2013.01); *C12N 9/96* (2013.01); *C12Q 1/6806* (2013.01); *C12Q 1/6874* (2013.01); *C12Q 2525/301* (2013.01); *C12Q 2565/50* (2013.01); *C12Q 2565/631* (2013.01); *C12Y 207/07007* (2013.01)

(58) Field of Classification Search
CPC .............. C12N 9/1247; G01N 2440/32
See application file for complete search history.

(56) References Cited

U.S. PATENT DOCUMENTS

| | | | |
|---|---|---|---|
| 8,936,911 B2 | 1/2015 | Sun | |
| 2004/0067492 A1 | 4/2004 | Peng | |
| 2006/0228325 A1 | 10/2006 | Wilbur | |
| 2007/0020654 A1 | 1/2007 | Blume | |
| 2012/0071359 A1 | 3/2012 | Sun | |
| 2012/0322666 A1 | 12/2012 | Pham | |
| 2013/0240356 A1 | 9/2013 | Wanunu | |
| 2014/0030704 A1 | 1/2014 | Mikawa | |
| 2014/0134610 A1 | 5/2014 | Pham | |
| 2014/0155276 A1* | 6/2014 | Pham ................ | C12Q 1/6869 506/26 |
| 2014/0193315 A1* | 7/2014 | Pham ............... | G01N 33/54313 422/561 |
| 2015/0167072 A1 | 6/2015 | Sun | |
| 2015/0218620 A1 | 8/2015 | Behlke | |
| 2015/0368710 A1 | 12/2015 | Fuller | |
| 2016/0011169 A1 | 1/2016 | Turner | |

FOREIGN PATENT DOCUMENTS

| | | |
|---|---|---|
| WO | 2006119439 A2 | 11/2006 |
| WO | 2009117698 A2 | 9/2009 |
| WO | 2012129242 | 9/2012 |
| WO | 2013019759 | 2/2013 |
| WO | 2014074727 A1 | 5/2014 |
| WO | 2015117163 A2 | 8/2015 |

(Continued)

OTHER PUBLICATIONS

Kumar et al., "PEG-Labeled Nucleotides and Nanopore Detection for Single Molecule DNA Sequencing by Synthesis," Scientific Reports, vol. 2, No. 684, pp. 1-8 (2012).
Anrather et al., "Supported Membrane Nanodevices," J. Nanoscience and Nanotechnology, vol. 4, No. 1/2, pp. 1-22 (2004).
Jorba et al., "Oligomerization of the influenza virus polymerase complex in vivo", J Gen Virol. Feb. 2008;89(Pt2):520-4. doi: 10.1099/vir.0.83387-0.
Stranges et al., "Design and characterization of a nanopore-coupled polymerase for single-molecule DNA sequencing by synthesis on an electrode array", Proc Natl Acad Sci U S A. Nov. 1, 2016;113(44):E6749-E6756. Epub Oct. 11, 2016.

(Continued)

*Primary Examiner* — Paul J Holland
(74) *Attorney, Agent, or Firm* — FisherBroyles, LLP; Victoria L. Boyd; Andrew K. Gonsalves

(57) ABSTRACT

Disclosed are methods for isolating polymerase complexes from a mixture of polymerase complex components. The polymerase complexes can comprise a nanopore to provide isolated nanopore sequencing complexes. The methods relate to the positive and negative isolation of the polymerase complexes and/or nanopore sequencing complexes. Also disclosed is a nucleic acid adaptor for isolating active polymerase complexes, polymerase complexes comprising the nucleic acid adaptor, and methods for isolating active polymerase complexes using the nucleic acid adaptor.

8 Claims, 16 Drawing Sheets

Specification includes a Sequence Listing.

(56) References Cited

FOREIGN PATENT DOCUMENTS

WO      2016154345      9/2016

OTHER PUBLICATIONS

Takahashi et al., Preparation of Phi29 DNA polymerase free of amplifiable DNA using ethidium monoazide, an ultraviolet-free light-emitting diode lamp and trehalose., PLoS One. Feb. 5, 2014;9(2):e82624. doi: 10.1371/journal.pone.0082624. eCollection 2014.

Zakeri, et al., "Peptide tag forming a rapid covalent bond to a protein, through engineering a bacterial adhesin", Proc Natl Acad Sci U S A. Mar. 20, 2012;109(12):E690-7. doi: 10.1073/pnas.1115485109. Epub Feb. 24, 2012.

* cited by examiner

PURIFICATION OF POLYMERASE COMPLEXES

CROSS-REFERENCE TO RELATED APPLICATIONS

This application is a divisional of U.S. patent application Ser. No. 15/989,109, filed May 24, 2018, which is a continuation of International Patent Application No. PCT/EP2016/078781, filed Nov. 25, 2016, which claims benefit of priority to U.S. Provisional Application No. 62/373,973, filed Aug. 11, 2016, to U.S. Provisional Application No. 62/295,010, filed Feb. 13, 2016 and to U.S. Provisional Application No. 62/260,194, filed Nov. 25, 2015, the contents of each of which are herein incorporated by reference in their entireties for all purposes.

SEQUENCE LISTING

The instant application contains a Sequence Listing which has been submitted electronically in ASCII format and is hereby incorporated by reference in its entirety. Said ASCII copy, created on May 6, 2020, is named SeqList04338527US2.txt and is 2 kilobytes in size.

TECHNICAL FIELD

Disclosed are methods for isolating polymerase complexes that are subsequently incorporated into membranes of biochips to enable nanopore sequencing of polynucleotides. Also disclosed is a nucleic acid adaptor for isolating active polymerase complexes, polymerase complexes comprising the nucleic acid adaptor, and methods for isolating active polymerase complexes using the nucleic acid adaptor.

BACKGROUND

Nanopore biochips are devices that provide single-molecule detection and analytical capabilities that are achieved by electrophoretically driving molecules in solution through a nano-scale pore. The nanopore provides a highly confined space within which single nucleic acid polymers can be analyzed at high throughput by one of a variety of means, and the perfect processivity that can be enforced in a narrow pore ensures that the native order of the nucleobases in a polynucleotide is reflected in the sequence of signals that is detected. Kilobase length polymers (single-stranded genomic DNA or RNA) or small molecules (e.g., nucleosides) can be identified and characterized without amplification or labeling, a unique analytical capability that makes inexpensive, rapid DNA sequencing a possibility.

DNA polymerases have been used in conjunction with nanopores to control the rate of DNA translocation through the nanopore. An enzyme motor coupled to a nanopore is attractive for two reasons: (1) the polymerase-DNA complex forms in bulk solution, enabling it to be electrophoretically captured in the nanopore; (2) relatively slow and controlled motion is observed as the polymerase processively steps the DNA molecule through the nanopore.

Progress has been made in providing engineered DNA polymerases with distinct functions and properties that refine the control of the movement of polynucleotide by the polymerases. However, a challenge remains in fabricating nanopore biochips that provide a high density of individually addressable nanopores that are functionally coupled to the polymerase-polynucleotide complexes.

BRIEF SUMMARY OF THE INVENTION

Disclosed are methods for isolating polymerase complexes from a mixture of polymerase complex components. The polymerase complexes can comprise a nanopore to provide isolated nanopore sequencing complexes. The methods relate to the positive and negative isolation of the polymerase complexes and/or nanopore sequencing complexes.

In one aspect, a method for isolating an active polymerase complex is provided. In some embodiments, the method comprises (a) providing a reaction mixture comprising unbound polymerase complex components, and a plurality of capture complexes each comprising a polymerase enzyme, a polynucleotide template, and a capture oligonucleotide conjugated to a purification moiety; (b) binding the capture complexes to a solid phase support comprising a purification moiety-binding compound; (c) providing reagents comprising nucleotides for enabling template complementary polynucleotide synthesis by the activity of the polymerase of the active polymerase complexes to obtain a plurality of active polymerase complexes comprising extended complementary sequences; and (d) isolating the active polymerase complexes having extended complementary sequences from inactive polymerase complexes comprising unextended complementary sequences, thereby isolating the active polymerase complexes. The inactive polymerase complexes having unextended complementary sequences remain bound to the solid phase support, and active polymerase complexes having extended complementary sequences are released from the capture complex by the activity of the polymerase.

In some embodiments, the polynucleotide template is a linear or a circular template, and the capture complexes each further comprise an oligonucleotide primer. In some embodiments, polynucleotide template is a self-priming template.

In some embodiments, the method further comprises removing unbound polymerase components from the capture complexes that are bound to the solid phase support.

In some embodiments, the binding of the capture complex to the solid phase medium is reversible.

In some embodiments, the purification moiety is a biotin or modified biotin, and the purification moiety-binding compound is streptavidin or modified streptavidin. In some embodiments, the biotin compound comprises desthiobiotin or a derivative thereof and the biotin-binding compound comprises streptavidin or a derivative thereof.

In some embodiments, the polymerase is selected from DNA polymerase, reverse transcriptase, and RNA polymerase. In some embodiments, the polymerase is a wild-type DNA polymerase or variant thereof.

In some embodiments, the isolated polymerase complexes each comprise a nanopore. In some embodiments, the nanopore is a wild-type nanopore or variant thereof. In some embodiments, the nanopore is a wild-type or a variant of an aHL or OmpG nanopore.

In another aspect, a method is provided for positively isolating a polymerase complex. In some embodiments, the method comprises (a) providing a reaction mixture comprising unbound polymerase complex components, and a plurality of capture complexes each comprising a polymerase enzyme, a polynucleotide template, and a capture oligonucleotide comprising a purification moiety; (h) binding the capture complexes to a solid support comprising a purification moiety-binding compound; and (c) isolating the polymerase complexes from the polymerase complex components.

In some embodiments, the polynucleotide template is a linear or a continuous template, and the capture oligonucleotide is a capture oligonucleotide primer. In some embodiments, the polynucleotide template is a self-priming template, and said self-priming template further comprises a purification moiety.

In some embodiments, the method further comprising releasing said polymerase-polynucleotide complex from the solid phase support.

In some embodiments, the method further comprises removing unbound polymerase components from the capture complexes that are bound to the solid phase support.

In some embodiments, the binding of the capture complex to the solid phase medium is reversible.

In some embodiments, the purification moiety is a biotin or modified biotin, and the purification moiety-binding compound is streptavidin or modified streptavidin. In some embodiments, the biotin compound comprises desthiobiotin or a derivative thereof and the biotin-binding compound comprises streptavidin or a derivative thereof.

In some embodiments, the polymerase is selected from DNA polymerase, reverse transcriptase, and RNA polymerase. In some embodiments, the polymerase is a wild-type DNA polymerase or variant thereof.

In some embodiments, the isolated polymerase complexes each comprise a nanopore. In some embodiments, the nanopore is a wild-type nanopore or variant thereof. In some embodiments, the nanopore is a wild-type or a variant form of an aHL or OmpG nanopore.

In another aspect, a method is provided for negatively isolating a polymerase complex from a mixed population of unbound polymerase complex components. In some embodiments, the method comprises: (a) providing a reaction mixture comprising polymerase complex components, and a plurality of polymerase complexes each comprising a polymerase enzyme bound to a polynucleotide template; (b) binding unbound polymerase enzyme to a capture oligonucleotide comprising a purification moiety to form a capture oligonucleotide polymerase enzyme composite; and (c) binding the capture oligonucleotide polymerase enzyme composite to a solid support comprising a purification moiety-binding compound, thereby isolating the polymerase complexes from the polymerase-polynucleotide complex components.

In some embodiments, the binding of the capture complex to the solid phase medium is reversible.

In some embodiments, the capture oligonucleotide is a double stranded polynucleotide. In some embodiments, the polynucleotide template is a linear or a circular template, and the capture complexes each further comprise an oligonucleotide primer. In some embodiments, the polynucleotide template is a self-priming template.

In some embodiments, the purification moiety is a biotin or modified biotin, and the purification moiety-binding compound is streptavidin or modified streptavidin. In some embodiments, the biotin compound comprises desthiobiotin or a derivative thereof, and the biotin-binding compound comprises streptavidin or a derivative thereof.

In some embodiments, the polymerase is selected from DNA polymerase, reverse transcriptase, and RNA polymerase. In some embodiments, the polymerase is a wild-type DNA polymerase or variant thereof.

In some embodiments, the isolated polymerase complexes each comprise a nanopore. In some embodiments, the nanopore is a wild-type nanopore or variant thereof. In some embodiments, the nanopore is a wild-type or a variant form of an aHL or OmpG nanopore.

In another aspect, a method is provided for preparing a biochip. In some embodiments, the method comprises (a) isolating a polymerase complex according to any one of the methods described herein; and (b) attaching the polymerase complex to a nanopore pre-formed in the membrane of the biochip to provide a nanopore-polymerase complex. In some embodiments, the membrane has a density of said nanopore sequencing complexes of at least 500,000 nanopore sequencing complexes 1 mm². In some embodiments, at least 70% of the nanopore-polymerase complexes are functional nanopore-polymerase complexes.

In other embodiments, the method provided for preparing a biochip comprises (a) isolating a polymerase complex according to any one of the methods described herein, wherein said polymerase complex further comprises a nanopore to provide a nanopore-polymerase complex; and (b) inserting the nanopore-polymerase complex into the membrane of the biochip. In some embodiments, the membrane has a density of said nanopore sequencing complexes of at least 500,000 nanopore sequencing complexes 1 mm². In some embodiments, at least 70% of the nanopore-polymerase complexes are functional nanopore-polymerase complexes.

In another aspect, provided herein is a biochip for sequencing polynucleotide templates. The biochip comprises an array of nanopore-polymerase complexes prepared according to any one of the methods described herein.

In another aspect, a method is provided for nanopore sequencing a polynucleotide template. The sequencing method comprises (a) preparing a biochip according to any one of methods described herein; (b) providing tagged nucleotides or nucleotide analogs to the nanopore sequencing complex, wherein the tag of the tagged nucleotide is detectable with the aid of the nanopore; (c) carrying out a polymerization reaction with the aid of the polymerase coupled to the nanopore of the nanopore-sequencing complex, thereby incorporating an individual nucleotide of the tagged nucleotides into a growing strand complementary to a sample polynucleotide template; and (d) detecting, with the aid of the nanopore, a tag associated with the individual tagged nucleotide during incorporation of said individual tagged nucleotide, wherein the tag is detected with the aid of the nanopore while the nucleotide is associated with the polymerase, thereby providing a sequence of the nucleic acid sample. In some embodiments, the polynucleotide template is single stranded DNA. In other embodiments, the polynucleotide template is double stranded DNA. In yet other embodiments, the polynucleotide template is RNA.

Nucleic Acid Adaptor for Isolating Active Polymerase Complexes and
Methods of Use Thereof Disclosed is a nucleic acid adaptor for isolating active polymerase complexes, polymerase complexes comprising the nucleic acid adaptor, and methods for isolating active polymerase complexes using the nucleic acid adaptor. The isolated polymerase complexes are subsequently incorporated into membranes of biochips to enable nanopore sequencing of polynucleotides.

In one aspect, a nucleic acid adaptor for isolating active polymerase complexes is provided. In some embodiments, the adaptor has a single-stranded region comprising a primer recognition sequence, a runway sequence located 5' to the primer recognition sequence, and a polymerase termination sequence located 5' to the runway sequence. In some embodiments, the runway sequence comprises a nucleotide sequence having between 2 and 50 contiguous nucleotide bases selected from no more than three of the four nucleotide bases of adenine, cytosine, guanine, and thymine, where the nucleotide base that is not contained in the runway sequence is designated as a stop base, and where the runway sequence functions as a template for polymerase-driven primer extension. In some embodiments, the polymerase termination sequence comprises at least one stop base that is effective to terminate any such polymerase-driven primer extension.

In some embodiments, the runway sequence is between 8 and nucleotide bases in length.

In some embodiments, the polymerase termination sequence is between 1 and 10 nucleotide bases in length.

In another aspect, a polymerase complex is provided. In some embodiments, the polymerase complex comprises: a nucleic acid adaptor as described herein; a primer specific to the primer recognition sequence of the adaptor; and a polymerase enzyme.

In another aspect, a method is provided for isolating active polymerase complexes. In some embodiments, the method comprises: (a) providing a reaction mixture comprising a polymerase complex as described herein and a nucleic acid sample, where the adaptor of the polymerase complex is ligated to said nucleic acid sample; (b) providing a deoxynucleotide triphosphate (dNTP) mixture comprising only those dNTPs that are complementary to the nucleotide bases contained in the runway sequence of the adaptor, where one or more of the dNTPs is modified to include a capture moiety having affinity to a binding partner; (c) combining the reaction mixture and the dNTP mixture to enable synthesis of a polynucleotide sequence complementary to the runway sequence by the activity of the polymerase to obtain a plurality of active polymerase complexes comprising extended runway complementary sequences having modified dNTPs incorporated therein; (d) binding said active polymerase complexes to a solid phase support, where the capture moieties of the modified dNTPs are bound to binding partners on the solid phase support; and (e) isolating said active polymerase complexes having extended runway complementary sequences from inactive polymerase complexes comprising unextended runway complementary sequences.

In some embodiments, the nucleic acid sample is a DNA or RNA sample.

In some embodiments, the isolating step comprises washing away the inactive polymerase complexes to yield active polymerase complexes bound to the solid phase support.

In some embodiments, the isolating step comprises washing away the inactive polymerase complexes to yield active polymerase complexes bound to the solid phase support, and thereafter eluting the active polymerase complexes from the solid phase support.

In some embodiments, the single-stranded region of the adaptor is a linear or a circular template.

In some embodiments, the binding step of the active polymerase complex to the solid phase support is reversible.

In some embodiments, the capture moiety is a biotin or modified biotin, and the binding partner is streptavidin or modified streptavidin. In some embodiments, the biotin compound comprises desthiobiotin or a derivative thereof, and the binding partner comprises streptavidin or a derivative thereof.

In some embodiments, the polymerase is selected from DNA polymerase, reverse transcriptase, and RNA polymerase. In some embodiments, the polymerase is a wild-type DNA polymerase or variant thereof.

In some embodiments, the isolated active polymerase complexes each comprise a nanopore. In some embodiments, the nanopore is a wild-type nanopore or variant thereof. In some embodiments, the nanopore is a wild-type or a variant of an aHL or OmpG nanopore.

In another aspect, a method is provided for preparing a biochip. In some embodiments, the method comprises: (a) isolating an active polymerase complex according to any one of the methods described herein; and (b) attaching the active polymerase complex to a nanopore pre-formed in the membrane of said biochip to provide a nanopore-polymerase complex. In some embodiments, the membrane has a density of said nanopore sequencing complexes of at least 500,000 nanopore sequencing complexes 1 $mm^2$. In some embodiments, at least 70% of the nanopore-polymerase complexes are functional nanopore-polymerase complexes.

In other embodiments, the method for preparing a biochip comprises: (a) isolating an active polymerase complex according any one of the methods described herein, where the active polymerase complex further comprises a nanopore to provide a nanopore-polymerase complex; and (b) inserting said nanopore-polymerase complex into the membrane of said biochip. In some embodiments, the membrane has a density of said nanopore sequencing complexes of at least 500,000 nanopore sequencing complexes 1 $mm^2$. In some embodiments, at least 70% of the nanopore-polymerase complexes are functional nanopore-polymerase complexes.

In another aspect, provided herein is a biochip for sequencing polynucleotide templates. The biochip comprises an array of nanopore-polymerase complexes prepared according to any one of the methods described herein.

In another aspect, a method is provided for nanopore sequencing a polynucleotide template. The sequencing method comprises: (a) preparing a biochip according to any one of methods described herein; (b) providing tagged nucleotides or nucleotide analogs to the nanopore sequencing complex, wherein the tag of the tagged nucleotide is detectable with the aid of the nanopore; (c) carrying out a polymerization reaction with the aid of the polymerase coupled to the nanopore of the nanopore-sequencing complex, thereby incorporating an individual nucleotide of the tagged nucleotides into a growing strand complementary to a sample polynucleotide template; and (d) detecting, with the aid of the nanopore, a tag associated with the individual tagged nucleotide during incorporation of said individual tagged nucleotide, where the tag is detected with the aid of the nanopore while the nucleotide is associated with the polymerase, thereby providing a sequence of the nucleic acid sample. In some embodiments, the polynucleotide template is single stranded DNA. In other embodiments, the polynucleotide template is double stranded DNA. In yet other embodiments, the polynucleotide template is RNA.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, if provided, like reference numerals contained in the drawings are meant to identify similar or identical elements.

DETAILED DESCRIPTION

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range. The term about is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention, which can be had by reference to the specification as a whole. Accordingly, the terms defined immediately below are more fully defined by reference to the specification as a whole.

All patents and publications, including all sequences disclosed within such patents and publications, referred to herein are expressly incorporated by reference.

Methods for nanopore sequencing of polymers e.g. polynucleotides and proteins, require enzyme-nanopore-polymer complexes positioned in a membrane e.g. a lipid bilayer, of a biochip.

Figure 1:
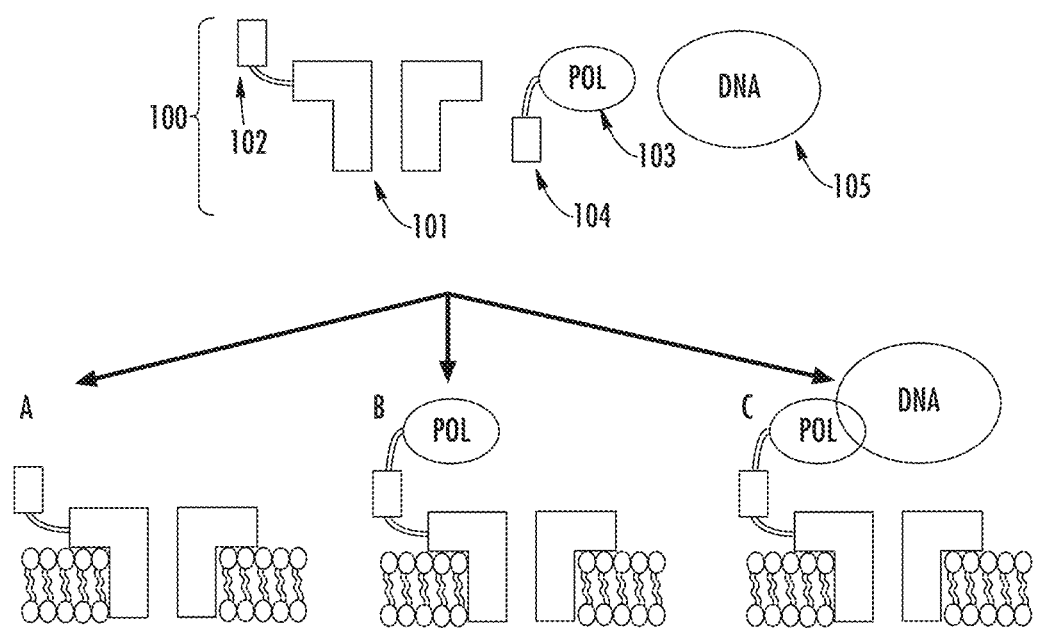
FIG. 1 depicts three possible nanopore structures that are inserted into a lipid bilayer from a mixture of nanopore protein, enzyme e.g. DNA polymerase, and substrate template e.g. DNA: bare nanopore (A), nanopore bound to polymerase (B), and nanopore bound to template-bound polymerase (C).

Current methods for providing an enzyme-nanopore-polymer complex comprise incubating nanopore protein, polymer, and enzyme to allow association of the components, flowing the reaction mixture onto a membrane, and either actively or passively reconstituting the resulting structures into the membrane. The three possible structures that become inserted into the membrane are: the nanopore alone, the nanopore associated with the enzyme, and the nanopore associated with the enzyme and polymer. For example, as shown in FIG. 1, flowing a reaction mixture (100) of nanopore (101) comprising an attachment component (102), polymerase enzyme (Pol) (103) comprising an attachment component (104), and polynucleotide (105) onto a lipid bilayer under conditions that will cause the nanopore to insert into the bilayer, e.g. electroporation, will result in (A) the nanopore alone being inserted into the bilayer, (B) the nanopore associated with the polymerase (enzyme-nanopore complex) being inserted into the bilayer, and (C) the nanopore-polymerase-polynucleotide template e.g. DNA, complex being inserted into the bilayer. Electroporation efficiency i.e. the efficiency of the process whereby diffusion of nanopore-polymerase-polynucleotide complexes diffuse to and are inserted into a membrane depends on the size of the nanopore complex. The larger the complex, the less the electroporation efficiency. Thus, of the three possible structures shown in FIG. 1, the nanopore alone (A) will diffuse more readily into the membrane than (B) nanopore-polymerase complex, which in turn, will diffuse more readily than (C) the nanopore-polymerase-polynucleotide complex. Efficiency will depend on the size-to-charge ratio of the complex. Structures A and B are non-functional as neither comprises all three components that are necessary to determine the sequence of the polymer e.g. DNA. Furthermore, A and B will occupy space on a biochip thereby diminishing the density of functional enzyme-nanopore-polymer complexes on a biochip. Additionally, at least a portion of the complexes having structure C will comprise polymerase enzyme that may not be active. Electroporation may be efficient in any size, but diffusion is believed to bring molecules to the membrane surface so that electroporation lowers the energy needed for the pore to enter the bilayer.

Provided herein are methods for selecting/isolating polymerase-polynucleotide complexes i.e. polymerase complexes, from mixtures of unbound complex components to minimize the formation of incomplete and/or inactive polymerase complexes in lipid bilayers, and thereby increase the efficiency of nanopore sequencing methods. The methods provided herein can be used to isolate polymerase complexes, which can be subsequently attached to nanopores inserted into the membrane of a biochip to form nanopore sequencing complexes. Additionally, the methods provided herein can be used to isolate polymerase complexes that further comprise a nanopore attached to the polymerase to form nanopore sequencing complexes that can subsequently inserted into the membrane of a biochip.

Definitions

The term "dNTP" refers to deoxynucleoside triphosphates. The purine bases (Pu) include adenine (A), guanine (G) and derivatives and analogs thereof. The pyrimidine bases (Py) include cytosine (C), thymine (T), uracil (U) and derivatives and analogs thereof. Examples of such derivatives or analogs, by way of illustration and not limitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminal, a terbium chelator such as N-(hydroxyethyl) ethylenediaminetriacetic acid that is capable of detection by delayed fluorescence, and the like.

The term "polymerase complex" herein refers to a complex formed by the association of a polymerase enzyme and a polynucleotide template substrate. Polynucleotide templates that are not self-priming require oligonucleotide primers to initiate strand extension. Accordingly, absent a self-priming polynucleotide, a polymerase complex can further include an oligonucleotide primer.

The term "active polymerase complex" herein refers to a complex that comprises an active polymerase capable of strand extension and a polynucleotide template. The active polymerase complex can further comprise a nanopore that is linked to the active polymerase to provide an active nanopore sequencing complex.

The term "nanopore sequencing complex" herein refers to a complex formed by association of a polymerase enzyme, a polynucleotide template substrate, and a nanopore. Polynucleotide templates that are not self-priming require oligonucleotide primers to initiate strand extension. Accordingly, absent a self-priming polynucleotide, a nanopore sequencing complex can further include an oligonucleotide primer.

The term "capture oligonucleotide" herein refers to an oligonucleotide that comprises a purification moiety that serves to immobilize polymerase complexes, nanopore sequencing complexes, or unbound polymerase and polymerase nanopore complexes to a solid support. Preferably, the purification moiety can be biotin or modified biotin, which binds to a purification moiety-binding partner e.g. streptavidin or modified streptavidin, on the solid support.

The term "functional" when used in reference to a nanopore sequencing complex, herein refers to a complex of three components: a nanopore inserted in a membrane, a polymer associated with an enzyme, and the polymer-associated enzyme that is attached to the nanopore in the membrane. The functional nanopores sequencing complex detects components of a sequence e.g. nucleotide bases of a polynucleotide.

The term "polymerase" herein refers to an enzyme that catalyzes the polymerization of nucleotide (i.e., the polymerase activity). The term polymerase encompasses DNA polymerases, RNA polymerases, and reverse transcriptases. A "DNA polymerase" catalyzes the polymerization of deoxynucleotides. An "RNA polymerase" catalyzes the polymerization of ribonucleotides. A "reverse transcriptase" catalyzes the polymerization of deoxynucleotides that are complementary to an RNA template.

The terms "polynucleotide" and "nucleic acid" are herein used interchangeably to refer to RNA, single stranded DNA (ssDNA), double stranded DNA (dsDNA), and cDNA molecules.

The term "template DNA molecule" herein refers to a strand of a nucleic acid from which a complementary nucleic acid strand is synthesized by a DNA polymerase, for example, in a primer extension reaction.

The term "sample polynucleotide" herein refers to a polynucleotide obtained from a sample e.g. a biological sample.

The term "template-dependent manner" refers to a process that involves the template dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: Molecular Biology of the Gene, 4th Ed., W. A. Benjamin, Inc., Menlo Park, Calif., (1987)).

The term "self-priming" herein refers to a polynucleptide template that generates a self-complementary sequence that can act as a primer for template-dependent extension by a polymerase e.g. a DNA polymerase. A hairpin template is an example of a self-priming template.

The term "nanopore" or "pore" as used herein, generally refers to a pore, channel or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha-hemolysin is an example of a protein nanopore.

The term "monomeric nanopore" herein refers to a nanopore protein that consists of a single subunit.

The term "oligomeric nanopore" herein refers to nanopores that can be composed of multiple identical subunits, multiple distinct subunits, or a mixture of identical and distinct subunits. Nanopores with identical subunits are termed "homo-oligomeric nanopores". Nanopores containing two or more distinct polypeptide subunits are termed "hetero-oligomeric nanopores".

The term "wild-type" herein refers to a gene or gene product that has the characteristics of that gene or gene product when isolated from a naturally occurring source.

The term "variant" herein refers to a modified protein which displays altered characteristics when compared to the parental protein, e.g., altered ionic conductance, altered time to thread, etc.

The term "modified variant" herein refers to a variant protein that has been further modified to alter its physical interaction with other proteins. For example, a modified variant protein may be a multimeric variant nanopore that has been further mutated to affect inter-subunit interactions.

The term "time to thread" or "TTT" herein refers to the time it takes the polymerase-tag complex to thread the tag into the nanopore.

The terms "noise" and "ionic current noise" are herein used interchangeably and refer to random fluctuations of electrical signal, which include current fluctuations contributed by spontaneous gating and current fluctuations contributed by the inherent architecture of the nanopore. For example, the tertiary make-up of the nanopore can comprise more than one recognition site for the analyte that is being sensed by the nanopore thereby inducing additional signals that contribute to the overall noise of the channel.

The term "constriction amino acids" herein refers to the amino acids that determine the size of a nanopore at the constriction zone. The constriction zone may be the same as the constriction zone of the wild-type nanopore or it may be a constriction zone introduced via protein engineering, or by the introduction of a molecular adapter.

The terms "alpha-hemolysin," "α-hemolysin," "aHL," "αHL," "a-HL" and "α-HL" are used interchangeably and herein refer to a protein that self-assembles into a heptameric water-filled transmembrane channel from monomers, concatemers of monomers, or a combination of monomers and concatemers of monomers.

The term "attachment component" herein refers to a structure e.g. a linker, which attaches the enzyme e.g. a polymerase, of an enzyme-polymer complex e.g. polymerase complex to a nanopore.

The terms "polynucleotide template" and "polynucleotide substrate template" herein refer to a polynucleotide molecule from which a complementary nucleic acid strand is synthesized by a polynucleotide polymerase e.g. DNA polymerase. The polynucleotide template can be linear, hairpin, or continuous. Continuous templates can be circular or dumbbell. Hairpin templates can be self-priming templates.

The term "polymerase complex components" herein refers to unbound components required to form a polymerase complex. The components include a polynucleotide template and a polymerase, and can further include an oligonucleotide primer, and/or a nanopore.

The term "isolated" herein refers to a polymerase complex or a nanopore sequencing complex that is separated from at least one of its unbound components from which it is ordinarily formed.

The term "purified" herein refers to a molecule that is present in a sample at a concentration of at least 95% by weight, or at least 98% by weight of the sample in which it is contained.

The term "purifying" generally refers to subjecting a polymerase complex or a nanopore sequencing complex to biochemical purification by affinity chromatography.

The term "nucleotide" herein refers to a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence," and is represented herein by a formula whose left to right orientation is in the conventional direction of 5'-terminus to 3'-terminus.

The term "modified nucleotide" herein refers to a nucleotide analog or a tagged nucleotide.

The term "nucleotide analog" herein refers to analogs of nucleoside triphosphates, e.g., (S)-Glycerol nucleoside triphosphates (gNTPs) of the common nucleobases: adenine, cytosine, guanine, uracil, and thymidine (Horhota et al. Organic Letters, 8:5345-5347 [2006]).

The term "tag" herein refers to a detectable moiety that may be atoms or molecules, or a collection of atoms or molecules. A tag may provide an optical, electrochemical, magnetic, or electrostatic (e.g., inductive, capacitive) signature, which may be detected with the aid of a nanopore.

The phrase "positively isolating" herein refers to a process of isolating a polymerase complex or a nanopore sequencing complex by binding the complex to a solid phase support, and removing unbound components.

The phrase "negatively isolating" herein refers to a process of isolating polymerase complex components from a reaction mixture comprising polymerase complexes and polymerase complex components, and binding the components to a solid phase support thereby isolating the polymerase complexes.

The term "biotin" as used herein are intended to refer to biotin (cishexahydro-2oxo-1H-thieno[3,4]imidazole-4-pentanoic acid) and any biotin derivatives and analogs. Such derivatives and analogues are substances which form a complex with the biotin binding pocket of native or modified streptavidin or avidin. Such compounds include, for example, iminobiotin, desthiobiotin and streptavidin affinity peptides, and also include biotin-.epsilon.-N-lysine, biocytin hydrazide, amino or sulfhydryl derivatives of 2-iminobiotin and biotinyl-ε-aminocaproic acid-N-hydroxysuccinimide ester, sulfo-succinimide-iminobiotin, biotinbromoacetylhydrazide, p-diazobenzoyl biocytin, 3-(N-maleimidopropionyl) biocytin. A preferred derivative of biotin to be used in the present invention is desthiobiotin or its derivative DSB-X Biotin, commercially available from Molecular Probes, Eugene, Oreg., USA; product number D20658)

The term "biotinylated" herein refers to a conjugate of modified biotin or biotin analogues with other moieties such as purification moieties e.g. nucleic acid molecules (including single or double stranded DNA, RNA, DNA/RNA chimeric molecules, nucleic acid analogs and any molecule which contains or incorporates a nucleotide sequence e.g., a peptide nucleic acid (PNA) or any modification thereof), proteins (including glycoproteins, enzymes, peptides library or display products and antibodies or derivatives thereof), peptides, carbohydrates or polysaccharides, lipids, etc., wherein the moieties are covalently linked to the modified biotin or biotin analogues. Many biotinylated ligands are commercially available or can be prepared by standard methods. Processes for coupling a biomolecule, e.g. a nucleic acid molecule or a protein molecule, to biotin are well known in the art (Bayer and Wilchek, Methods in Molec. Biology 10, 143. 1992).

The term "binding partner" is defined as any biological or other organic molecule capable of specific or non-specific binding or interaction with another biological molecule, which binding or interaction may be referred to as "ligand" binding or interaction and is exemplified by, but not limited to, antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector or repressor/inducer bindings or interactions. The term "binding partner" herein refers to the partners of an affinity complex e.g. modified biotin-modified biotin binding partner, used in the isolation methods described herein.

The term "conjugate" as used herein refer to any conjugate comprising a biotin compound and a biotin-binding compound, in which the biotin compound and biotin-binding compound are linked by non-covalent bonding. Typically, biotin will be bound or linked to one or more, preferably one, biological or chemical entity, e.g. a biomolecule. As explained above, such biotin compounds containing biotin linked to other entities are also referred to herein as "biotinylated" purification moieties.

The term "biotin-binding" compound as used herein is intended to encompass any compound which is capable of tightly but non-covalently binding to biotin or any biotin compound. Preferred biotin-binding compounds include modified streptavidin and avidin, as well as derivatives and analogues thereof e.g. nitro-streptavidin.

The term "avidin" as used herein refers to the native egg-white glycoprotein avidin as well as derivatives or equivalents thereof, such as deglycosylated or recombinant forms of avidin, for example, N-acyl avidins, e.g., N-acetyl, N-phthalyl and N-succinyl avidin, and the commercial products ExtrAvidin, Neutralite Avidin and CaptAvidin The term "streptavidin" as used herein refers to bacterial streptavidins produced by selected strains of *Streptomyces*, e.g., *Streptomyces avidinii*, as well as derivatives or equivalents thereof such as recombinant and truncated streptavidin, such as, for example, "core" streptavidin.

The terms "reversible" and "releasable" are used herein interchangeably and are intended to mean physical separation or detachment or dissociation of the partners of an affinity complex e.g. modified biotin-modified biotin binding partner. What is required, is that the linkage between the modified biotin and the modified biotin-binding partner is disrupted or broken to allow separation of the respective entities.

The term "displacer" herein refers to a molecule (for example, free biotin) that may physically break or destabilize the linkage between partners of an affinity complex e.g. modified biotin-modified biotin binding partner, in a sufficient manner to allow it to be cleaved, or reversed, thus allowing the two linked entities to be separated.

The terms "runway" or "runway sequence" herein refer to a nucleotide sequence that is composed of three of the four nucleotides (i.e., any combination of three nucleotides selected from A, T, G, and C). This runway section can be 3 to 50 bases long, preferably 8 to 12 bases.

In one aspect, the present invention provides a method for isolating active polymerase complexes, said method comprising:

(a) providing a reaction mixture comprising unbound polymerase complex components, and a plurality of capture complexes each comprising a polymerase enzyme, a polynucleotide template, and a capture oligonucleotide conjugated to a purification moiety;

(b) binding said capture complexes to a solid phase support comprising a purification moiety-binding compound;

(c) providing reagents comprising nucleotides for enabling template complementary polynucleotide synthesis by the activity of the polymerase of said active polymerase complexes to obtain a plurality of active polymerase complexes comprising extended complementary sequences; and (d) isolating said active polymerase complexes having extended complementary sequences from inactive polymerase complexes comprising unextended complementary sequences and capture oligonucleotides, thereby isolating said active polymerase complexes from said polymerase complex components.

The inactive polymerase complexes having unextended complementary sequences may remain bound to said solid phase support, and active polymerase complexes having extended complementary sequences may be released from said capture complex by the activity of said polymerase.

In a second aspect, the present invention provides a method for positively isolating a polymerase complex, said method comprising:

(a) providing a reaction mixture comprising unbound polymerase complex components, and a plurality of capture complexes each comprising a polymerase enzyme, a polynucleotide template, and a capture oligonucleotide comprising a purification moiety;

(b) binding said capture complexes to a solid support comprising a purification moiety-binding compound; and (c) isolating said polymerase complexes from said polymerase complex components.

Said polynucleotide template may be a linear or a continuous template, and the capture oligonucleotide may be a capture oligonucleotide primer. Said template may also be a self-priming template, and said self-priming template further comprises a purification moiety. The method may also comprise a step of, further comprising releasing said polymerase-polynucleotide complex from said solid phase support.

In a third aspect, the present invention provides a method for negatively isolating a polymerase complex from a mixed population of unbound polymerase complex components, said method comprising:

(a) providing a reaction mixture comprising polymerase complex components, and a plurality of polymerase complexes each comprising a polymerase enzyme bound to a polynucleotide template;

(b) binding unbound polymerase enzyme to an optionally double stranded capture oligonucleotide comprising a purification moiety to form a capture oligonucleotide polymerase enzyme composite; and (c) binding said capture oligonucleotide polymerase enzyme composite to a solid support comprising a purification moiety-binding compound, thereby isolating said polymerase complexes from said polymerase-polynucleotide complex components.

The polynucleotide template according to the methods above may be a linear or a circular template, and the capture complexes may each further comprise an oligonucleotide primer. The polynucleotide template also be a self-priming template. The methods above may further comprise a step of removing unbound polymerase components from said capture complexes bound to said solid phase support. The binding of said capture complex to said solid phase medium may be reversible. The purification moiety may be a biotin or modified biotin, and said purification moiety-binding compound may be streptavidin or modified streptavidin. Said biotin compound may comprise desthiobiotin or a derivative thereof, and said biotin-binding compound may comprise streptavidin or a derivative thereof. The polymerase may be a DNA polymerase, a reverse transcriptase or a RNA polymerase either as a wild-type DNA polymerase or as a variant thereof. The isolated polymerase complexes may each comprise a nanopore, which may be a wild-type nanopore or variant thereto such as a wild-type or a variant of an aHL or OmpG nanopore.

In a fourth aspect, the present invention provides a method for preparing a biochip, said method comprising:

(a) isolating a polymerase complex according to any one of the methods disclosed above, and (b) attaching said polymerase complex to a nanopore pre-formed in the membrane of said biochip to provide a nanopore-polymerase complex, or (b) inserting said nanopore-polymerase complex into the membrane of said biochip.

Said membrane may have a density of said nanopore sequencing complexes of at least 500,000 nanopore sequencing complexes 1 mm². At least 70% of the nanopore-polymerase complexes are functional nanopore-polymerase complexes.

The biochip may be a biochip for sequencing polynucleotide templates comprising an array of nanopore-polymerase complexes prepared as disclosed above.

In a fifth aspect, the present invention provides a method for nanopore sequencing a polynucleotide template, comprising:

(a) preparing a biochip according to any one of claims 20 and 21;

(b) providing tagged nucleotides or nucleotide analogs to said nanopore sequencing complex, wherein the tag of said tagged nucleotide is detectable with the aid of said nanopore;

(c) carrying out a polymerization reaction with the aid of said polymerase coupled to said nanopore in said nanopore-sequencing complex, thereby incorporating an individual tagged nucleotide of said tagged nucleotides into a growing strand complementary to a sample polynucleotide template; and (d) detecting, with the aid of said nanopore, a tag associated with said individual tagged nucleotide during incorporation of said individual tagged nucleotide, wherein said tag is detected with the aid of said nanopore while said nucleotide is associated with said polymerase, thereby providing a sequence of said nucleic acid sample.

The polynucleotide template may be single stranded DNA, double stranded DNA, or RNA.

In a sixth aspect, the present invention provides a nucleic acid adaptor for isolating active polymerase complexes, said adaptor having a single-stranded region comprising a primer recognition sequence, a runway sequence located 5' to the primer recognition sequence, and a polymerase termination sequence located 5' to the runway sequence, wherein said runway sequence comprises a nucleotide sequence having between 2 and 50 contiguous nucleotide bases selected from no more than three of the four nucleotide bases of adenine, cytosine, guanine, and thymine, wherein the nucleotide base that is not contained in the runway sequence is designated as a stop base, and wherein said runway sequence functions as a template for polymerase-driven primer extension, and wherein said polymerase termination sequence comprises at least one stop base that is effective to terminate any such polymerase-driven primer extension.

The runway sequence may be between 8 and 12 nucleotide bases in length, whereas the polymerase termination sequence may be between 1 and 10 nucleotide bases in length.

The nucleic acid adaptor may be part of a polymerase complex further comprising a primer specific to the primer recognition sequence of the adaptor; and a polymerase enzyme.

In a seventh aspect, the present invention provides a method for isolating active polymerase complexes, said method comprising:

(a) providing a reaction mixture comprising a polymerase complex isolated as disclosed above and a nucleic acid DNA or RNA sample, wherein the adaptor of the polymerase complex is ligated to said nucleic acid sample;

(b) providing a deoxynucleotide triphosphate (dNTP) mixture comprising only those dNTPs that are complementary to the nucleotide bases contained in the runway sequence of the adaptor, wherein one or more of the dNTPs is modified to include a capture moiety having affinity to a binding partner;

(c) combining the reaction mixture and the dNTP mixture to enable synthesis of a polynucleotide sequence complementary to the runway sequence by the activity of the polymerase to obtain a plurality of active polymerase complexes comprising extended runway complementary sequences having modified dNTPs incorporated therein;

(d) binding said active polymerase complexes to a solid phase support, wherein the capture moieties of the modified dNTPs are bound to binding partners on the solid phase support; and (e) isolating said active polymerase complexes having extended runway complementary sequences from inactive polymerase complexes comprising unextended runway complementary sequences.

The method may comprise a step of washing away the inactive polymerase complexes to yield active polymerase complexes bound to the solid phase support. Thereafter, the active polymerase complexes may be eluted from the solid phase support. Said single-stranded region of the adaptor may be a linear or a circular template. Binding of said active polymerase complex to said solid phase support may be reversible. The capture moiety may be a biotin or modified biotin, and said binding partner may be streptavidin or modified streptavidin. For example, said biotin compound may comprise desthiobiotin or a derivative thereof, and said binding partner may comprises streptavidin or a derivative thereof. The polymerase is wildtype or variant DNA polymerase, reverse transcriptase, or a RNA polymerase. The isolated active polymerase complexes may each comprise a wild-type nanopore or variant thereof, for example a wild-type or a variant of an aHL or OmpG nanopore.

In an eighth aspect, the present invention provides a method for preparing a biochip, comprising the steps of
(a) isolating an active polymerase complex as disclosed above; and
(b) attaching said active polymerase complex to a nanopore pre-formed in the membrane of said biochip to provide a nanopore-polymerase complex or
(b) inserting said nanopore-polymerase complex into the membrane of said biochip.

The membrane may have a density of said nanopore sequencing complexes of at least 500,000 nanopore sequencing complexes 1 mm$^2$. At least 70% of the nanopore-polymerase complexes should be functional nanopore-polymerase complexes.

The present invention is also directed to a biochip for sequencing polynucleotide templates, comprising an array of nanopore-polymerase complexes prepared as disclosed above.

In a final aspect, the present invention provides a method for nanopore sequencing a polynucleotide template, said method comprising:
(a) preparing a biochip as disclosed above;
(b) providing tagged nucleotides or nucleotide analogs to said nanopore sequencing complex, wherein the tag of said tagged nucleotide is detectable with the aid of said nanopore;
(c) carrying out a polymerization reaction with the aid of said polymerase coupled to said nanopore in said nanopore-sequencing complex, thereby incorporating an individual tagged nucleotide of said tagged nucleotides into a growing strand complementary to a sample polynucleotide template; and
(d) detecting, with the aid of said nanopore, a tag associated with said individual tagged nucleotide during incorporation of said individual tagged nucleotide, wherein said tag is detected with the aid of said nanopore while said nucleotide is associated with said polymerase, thereby providing a sequence of said nucleic acid sample.

The polynucleotide template may be double stranded DNA, is single stranded DNA or RNA.

Methods for Isolating Polymerase Complexes and/or Nanopore Sequencing Complexes:

Displacement Purification—Method for Isolating Active Polymerase Complexes and/or Active Nanopore Sequencing Complexes:

In one aspect, a method is provided for preparing an active nanopore sequencing complex comprising an active polymerase associated with a polynucleotide template i.e. an active polymerase complex. In some embodiments, the active polymerase of the polymerase complex is bound to a nanopore. The active nanopore complex is formed by the binding of its components that are provided as a mixture. The active polymerase complex comprises a polymer template substrate e.g. a polynucleotide template, and an active polymerase bound to the template. The active polymerase complex can further comprise a nanopore that is bound to the active polymerase. The formed active polymerase complex is subsequently isolated from the mixture of unbound polymerase complex components, and inactive polymerase complexes. Unbound polymerase components comprise distinct polymerase enzyme molecules, template molecules, and nanopore proteins, and nanopore proteins that have associated with polymerase enzyme, but not with template molecules. Active polymerase complexes are isolated from inactive polymerase complexes by the ability of the polymerase to incorporate nucleotides into a polynucleotide strand in a template-dependent sequence, which displaces a capture oligonucleotide that is hybridized to the polynucleotide template. The process of polymerase-dependent displacement of a capture oligonucleotide from the polynucleotide template is illustrated in FIG. 2.

Figure 2:
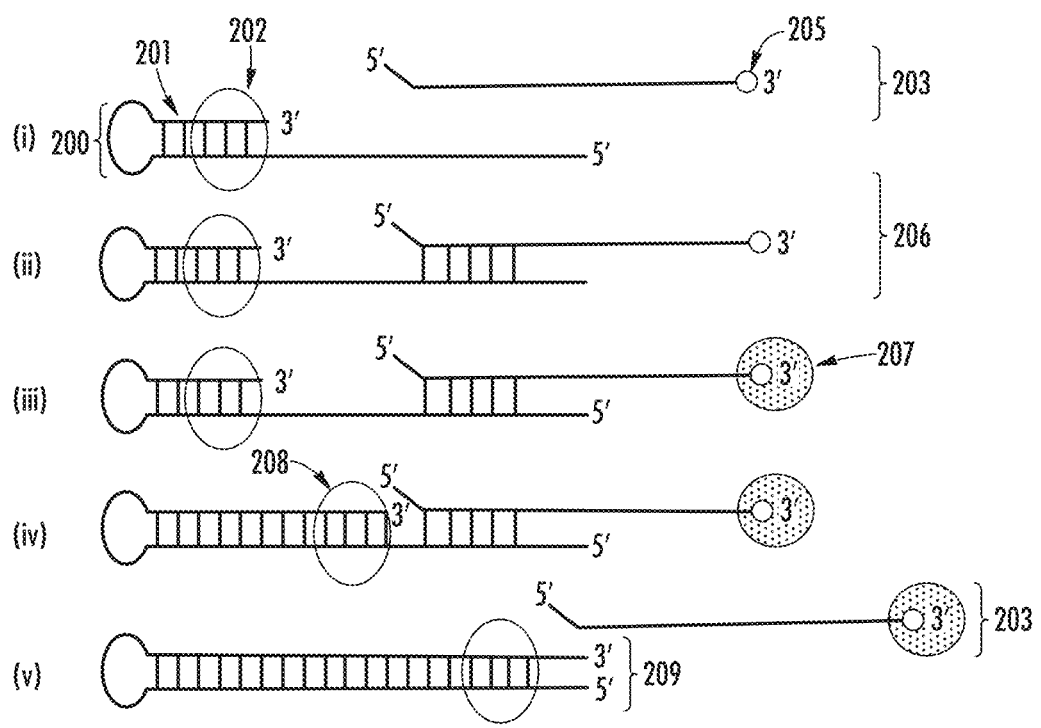
FIG. 2 illustrates the process for obtaining of an active polymerase complex by active displacement of a capture oligonucleotide.

FIG. 2 illustrates a polymerase complex that comprises a self-priming template (201) and a polymerase (202) bound to the double stranded portion of the self-priming template. In a first step (i), the polymerase complex combines with a capture oligonucleotide (203), which comprises a polynucleotide (204) and a purification moiety (205), to form a capture complex (206) in step (ii). The capture complex is tethered/bound to a solid phase (207) by means of the purification moiety of the capture oligonucleotide (203) in step (iii). The interaction of the capture oligonucleotide with the polymerase complex occurs by hybridization of sequences on the template and the oligonucleotide. Under catalytic conditions comprising nucleotides and MgCl$_2$, in step (iv), the active polymerase (208) extends the self-priming template, which as it reaches the bound capture oligonucleotide, displaces the capture oligonucleotide from the capture complex as shown in step (v). The free capture oligonucleotide (203) remains bound to the solid phase support, and the active polymerase complex (209) is isolated from inactive polymerase complexes and released capture oligonucleotides. An inactive polymerase complex fails to extend the self-priming template, and the polymerase complex remains bound to the capture oligonucleotide as is shown in (iii).

Figure 3:
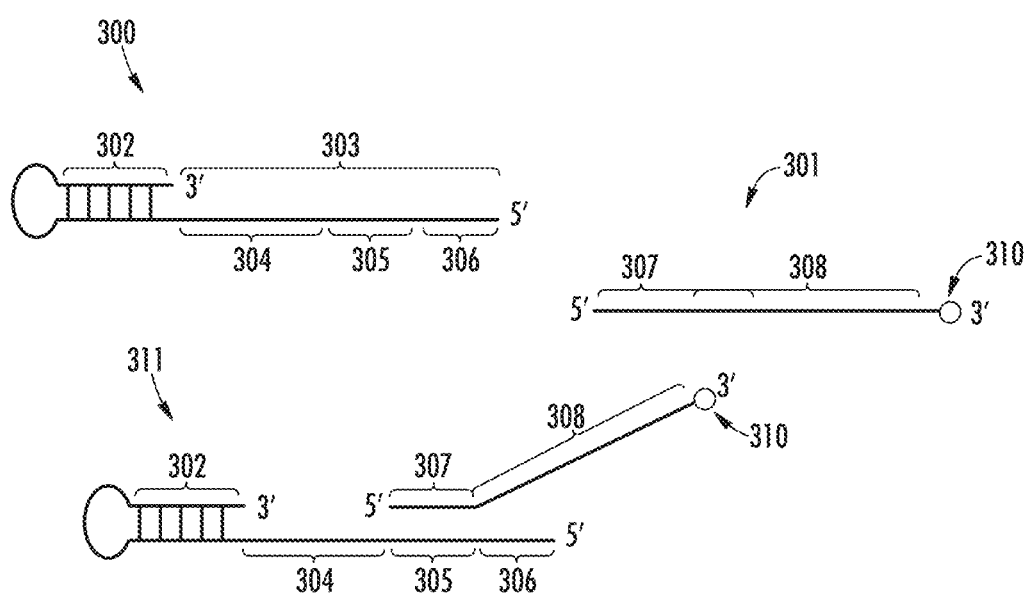
FIG. 3 illustrates the formation of a capture complex comprising a self-primed polynucleotide and a capture oligonucleotide.

The structure of the capture complex provided in FIG. 2 is shown in detail in FIG. 3. In this exemplary illustration, the self-priming hairpin polynucleotide template (300), which is hybridized to a capture oligonucleotide (301), to form a template-capture oligonucleotide complex (311). The polynucleotide template (300) comprises a region of self-complementary double stranded region (302), and a 5' overhang sequence (303), which comprises a first (304), second (305) and third (306) sequences. First sequence (304) serves as template sequence that directs the complementary extension of the 3' end of the template. Second sequence (305) comprises nucleotides that are complementary to the nucleotide bases of sequence 307 of the capture oligonucleotide. Third sequence (306) comprises four known nucleotide bases that serve to pause polymerase synthesis of the complementary strand. The capture oligonucleotide (301) comprises a first sequence (307), which is complementary to the second sequence of the polynucleotide template (305), and to which the capture oligonucleotide hybridizes; and a second linker sequence (308), which comprises a purification moiety (310) at its 3' end. The purification moiety links/tethers the template-capture oligonucleotide complex to a purification moiety (310). As described for FIG. 1, a polymerase enzyme associates with the double stranded template region (302), and under catalytic conditions, an active polymerase extends the 3' end of the template to incorporate nucleotide bases that are complementary to the bases of sequence 304. As the active polymerase reaches the region of hybridization between the capture oligonucleotide (307) and the template (305), the capture oligonucleotide is displaced from the active polymerase-template complex. An inactive polymerase will not extend the 3' end of the template, and will fail to displace the capture oligonucleotide. The purification moiety is subsequently bound to a solid phase medium thereby isolating inactive polymerase-template complexes and displaced capture oligonucleotides from the remaining active-polymerase complexes.

Sequence 306 of the template polynucleotide comprises a stop sequence, which is designed/used to pause the activity of the active polymerase of the active polymerase-template complex. A stop sequence can be a sequence of four nucleotide bases, wherein the fourth base is different from the first three bases. As the polymerase reaches the stop sequence, only the nucleotide bases that are complementary to the first three of the corresponding template bases are provided to pause the active polymerase. The active-polymerase-template complex is subsequently inserted in the membrane of a biochip, where it is reactivated by providing the nucleotide base that is complementary to the fourth base of the stop sequence (307), to allow for nanopore sequencing of the template. In some embodiments, the active sequencing complex comprises a nanopore the active polymerase is pre-bound to a nanopore, and the nanopore-polymerase-template complex is subsequently inserted into the membrane of the biochip. In other embodiments, the active polymerase is not prebound to a nanopore, and the polymerase-template complex is bound to a nanopore that is pre-inserted in the membrane of a biochip.

Figure 4:
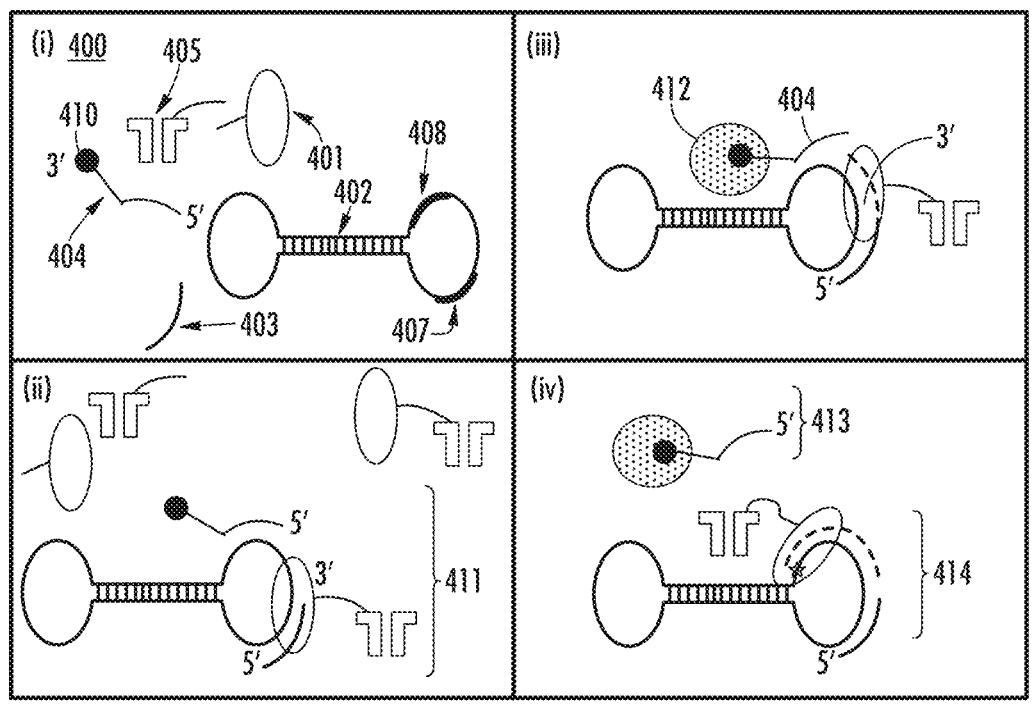
FIG. 4 illustrates a process for isolating an active polymerase complex from a mixture of polymerase complex components.

FIG. 4 illustrates an example of the method for preparing active nanopore sequencing complexes. In this example, the polynucleotide template is a continuous polynucleotide template, which is in the form of a dumbbell. The polynucleotide template structure can be linear, continuous e.g. circular, or hairpin. Linear and circular templates require a primer oligonucleotide to prime polymerization of the complementary strand, while hairpin templates are self-priming and do not require the primer oligonucleotide. The method includes (i) providing a solution comprising a mixture (400) of polymerase enzyme (401), polynucleotide template (402), oligonucleotide primer (403), capture oligonucleotide (404), and optionally, nanopore (405). The nanopore, when provided at this step, can be attached to the polymerase as a nanopore-polymerase complex (406). The polynucleotide template comprises a first nucleotide sequence (407) that is complementary to that of an oligonucleotide primer (403), and a second nucleotide sequence (408) that is complementary to a portion (409) of the sequence of capture oligonucleotide (404). Optionally, the template includes a nucleotide sequence that encodes a stop sequence (409), which halts polymerization of the complementary strand by the active polymerase. The capture oligonucleotide comprises at its 3' end a purification moiety (410) that enables removal of inactive polymerase-template complexes as described in the following.

In (ii), in the absence of magnesium and dNTPs, i.e. under non-catalytic conditions, a capture complex (411) comprising a polynucleotide template, an oligonucleotide primer, a polymerase enzyme, and a capture oligonucleotide is formed. In some embodiments, the capture complex does not include the nanopore, In (iii), the nanopore sequencing complex is bound to a solid phase medium (412) to which it is tethered by the capture oligonucleotide. Uncomplexed components i.e. nanopore, polymerase, and nanopore-bound polymerase are removed, and under catalytic conditions e.g. Mg Cl2 and dNTPs, an active polymerase extends the primer sequence and displaces the solid-phase bound capture oligonucleotide (413), as shown in (iv). Strand synthesis proceeds until polymerization is halted/paused. In the exemplary process shown in FIG. 4, polymerization can be paused with EDTA. Alternatively, polymerization can be paused by the stop-sequence comprised in the polynucleotide template as shown in FIG. 3, The active nanopore-sequencing complex (414) is subsequently isolated from the solid-phase bound capture oligonucleotide (413), and is inserted in a membrane e.g. a lipid membrane, of a biochip where nanopore sequencing of the template is performed. In some embodiments, the isolated active polymerase-complex does not comprise a nanopore, and the isolated active polymerase complex is bound to a nanopore that is pre-inserted in the membrane of a biochip.

Figure 5:
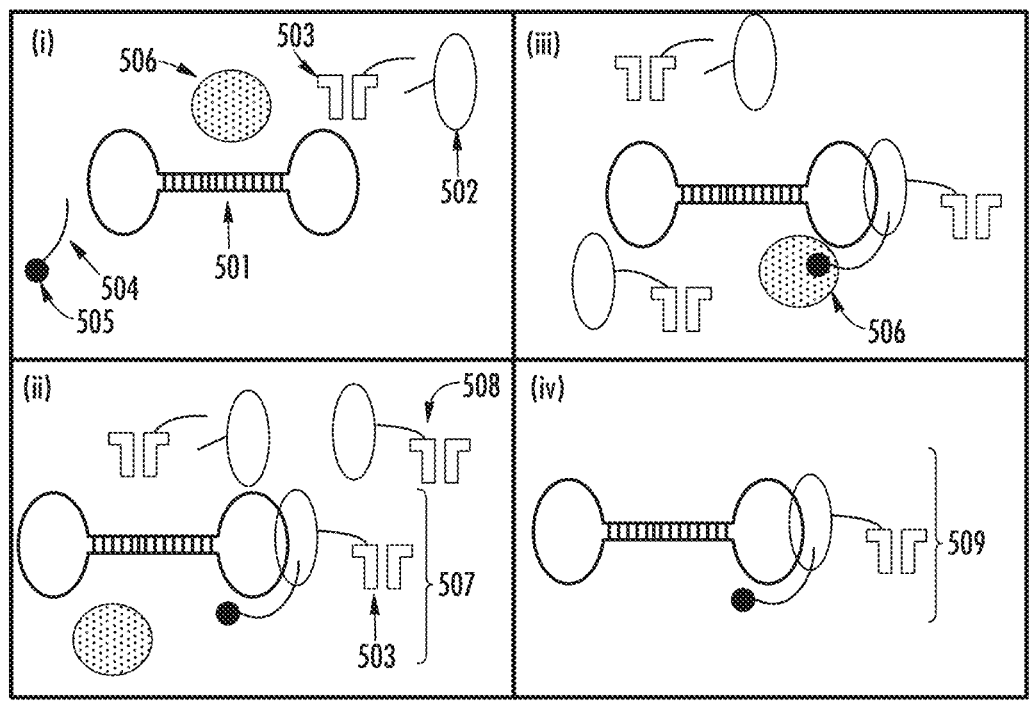
FIG. 5 illustrates a process for positively isolating a polymerase complex from a mixture of polymerase complex components.

Positive Isolation of Polymerase Complexes and/or Nanopore Sequencing Complexes:

In another aspect, a polymerase complex is isolated from its components, by positively isolating the polymerase complex by binding the complex to a solid phase support. In this instance, the polymerase complex is part of the capture complex. An example of a method for positively isolating a polymerase complex is shown in FIG. 5.

In a first step (i), polymerase complex components are provided in a reaction mixture, and are incubated to allow for their association to form a polymerase complex. In some embodiments, the components in the reaction mixture comprise polynucleotide templates (501) and polymerase enzyme (502). In other embodiments, the components of the reaction mixture further comprise nanopore proteins (503). In embodiments wherein the polynucleotide templates are self-priming templates, no oligonucleotide primers are included in the reaction mixture, and a purification moiety is attached to the 5' end of the templates. In embodiments, wherein the polynucleotide templates are linear or circular, oligonucleotide primers (504) are included. The oligonucleotide primers comprise a purification moiety (505). A solid phase support (506) comprising a purification moiety-binding compound can be added at this step, or it can be added in subsequent step (ii). FIG. 5 illustrates the method that uses an oligonucleotide primer as the capture oligonucleotide.

Subsequently (ii), polymerase complexes (507) are formed by association of polynucleotide template, oligonucleotide primer comprising a purification moiety, and polymerase enzyme bound to the double stranded template-primer region. In some embodiments, as shown in FIG. 5, the polymerase enzyme of the complex is linked to a nanopore protein (503). Association between nanopore and polymerase can occur to form a nanopore-polymerase complex (508), which may not be incorporated into the polymerase complex.

As shown in (iii), the polymerase complex is purified from polymerase components by binding to a solid phase support (506). The unassociated/unbound components are removed, leaving the polymerase complexes bound to the solid phase support, which can be eluted from the solid phase support to obtain the isolated polymerase complexes (509). Polymerase complexes having a nanopore attached to the polymerase enzyme component can be subsequently inserted into a membrane of a biochip where sequencing of the template can proceed as described elsewhere herein. Alternatively, polymerase complexes lacking the nanopore can be attached to nanopores that are pre-inserted into the membrane of a biochip.

Figure 6:
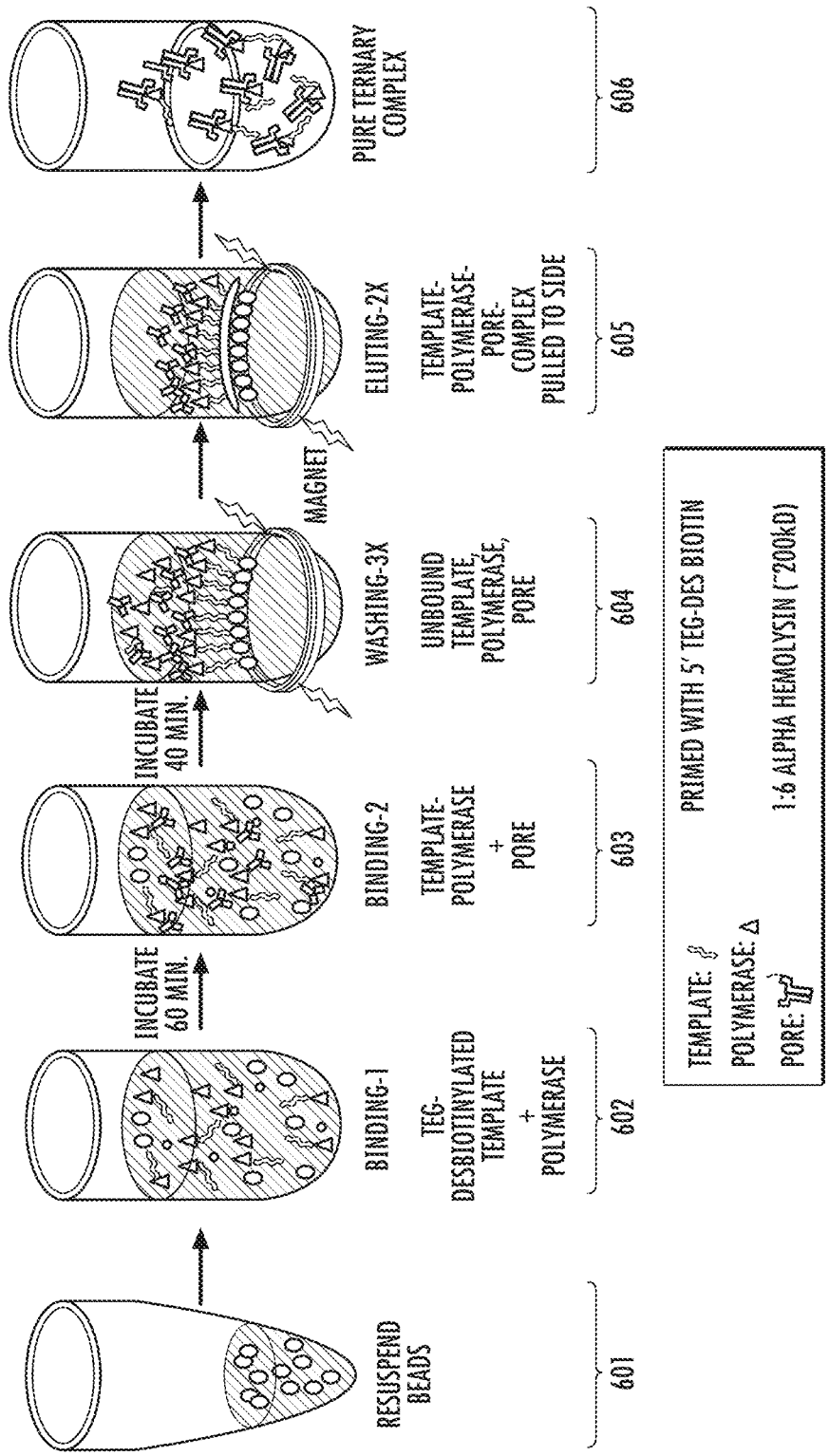
FIG. 6 illustrates an embodiment of a process for positively isolating a polymerase complex from a mixture of polymerase complex components.

FIG. 6 illustrates an embodiment of the positive isolation process described in FIG. 5. In the process shown in FIG. 6, the solid phase support e.g. magnetic beads (501), coated with streptavidin are reacted with a polynucleotide template having a desthiobiotin purification moiety, and a polymerase e.g. DNA polymerase (602). The template that is complexed with polymerase enzyme and pore (603), binds to the streptavidin beads. Unbound polymerase complex components are washed away (605), and the polymerase complex comprising template, polymerase and nanopore is eluted (606) from the streptavidin beads to provide a purified nanopore sequencing complex i.e. a pure ternary complex (607). FIG. 6 shows that the solid phase support may be added in the mixture of polymerase complex components. Therefore, it is optional that formation of polymerase complexes be allowed to occur prior to adding the solid phase support.

Figure 7:
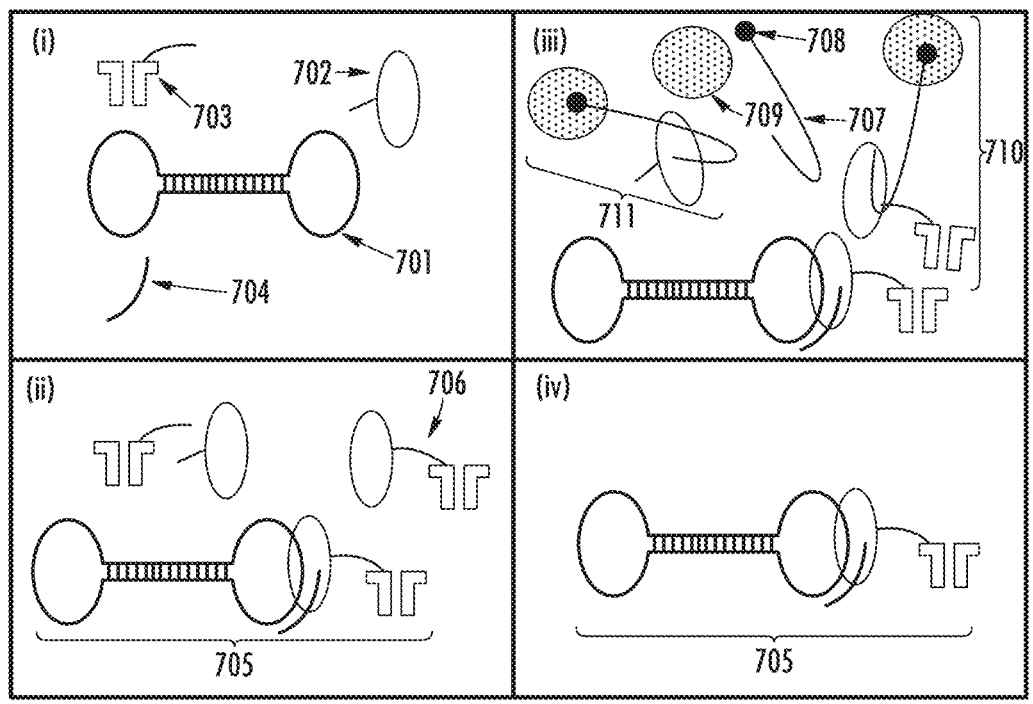
FIG. 7 illustrates a process for negatively isolating a polymerase complex from a mixture of polymerase complex components.

Negative Isolation of Polymerase Complexes and/or Nanopore Sequencing Complexes:

In another aspect, a polymerase complex is isolated from its components, by negatively isolating the polymerase complex by binding unassociated complex components to a solid phase support and collecting the polymerase complex from the unbound fraction of the reaction mixture. In this instance, the polymerase components are part of the capture complex. An example of a method for negatively isolating a polymerase complex is shown in FIG. 7.

In a first step (1), polymerase complex components are provided in a reaction mixture, and are incubated to allow for their association to form a polymerase complex. In some embodiments, the components in the reaction mixture comprise polynucleotide templates (701) and polymerase enzyme (702). In other embodiments, the components of the reaction mixture further comprise nanopore proteins (703). In embodiments wherein the polynucleotide templates are self-priming templates e.g. hairpin templates, no oligonucleotide primers are included in the reaction mixture. In embodiments, wherein the polynucleotide templates are linear or continuous e.g. circular, oligonucleotide primers (704) are included. FIG. 7 illustrates the method that uses an oligonucleotide as the capture oligonucleotide. The capture oligonucleotide can be a self-priming polynucleotide that associates with polymerase enzyme component.

Association of polymerase complex components results in the formation of a polymerase complex comprising a polynucleotide template and a polymerase enzyme. In the example shown in FIG. 7 (ii), the template is continuous, and the polymerase complex further comprises an oligonucleotide primer (705). When present in the reaction mixture, nanopore components can associate with free polymerase components to form free nanopore-polymerase complexes (606). Subsequently, as shown in FIG. 7 (iii), a capture oligonucleotide (707) comprising a purification moiety (708) and a solid phase support (709) are added to the reaction mixture. The capture oligonucleotide can be a self-priming polynucleotide that associates with free polymerase enzyme component, and/or with polymerase-nanopore complex when nanopore is included in the reaction mixture to form capture complexes (710) and (711), respectively. The solid phase support (709) binds the purification moiety of the capture complexes providing an unbound fraction that is enriched with polymerase complex (705).

Polymerase complexes comprising a nanopore (713) attached to the polymerase enzyme can be subsequently inserted into a membrane of a biochip where sequencing of the template can proceed as described elsewhere herein. Alternatively, polymerase complexes lacking the nanopore can be attached to nanopores that are pre-inserted into the membrane of a biochip.

Purification Moiety and Purification Moiety-Binding Partner/Ligands:

Methods for isolating a polymerase complex from free or unbound polymerase complex components include affinity chromatography, also known as affinity purification.

In some embodiments, affinity purification is employed in the process of positive isolation of the polymerase complex whereby the polymerase complex is coupled to a solid support via the binding of a purification moiety of the polymerase complex to a purification moiety-binding partner on the solid phase support. The free or unbound complex components are washed away, and the solid support-bound polymerase complex is subsequently eluted from the solid support to provide a purified polymerase complex fraction. In some embodiments, the binding of the polymerase complex to the solid phase support is reversible. The process is described with reference to b.

In other embodiments, affinity purification is employed in the process of negative isolation of the polymerase complex components whereby the unwanted, unbound components of a polymerase complex are removed from the desired polymerase complex by the binding of a purification moiety of the unbound components to a purification moiety-binding ligand of the solid phase support. In some embodiments, the binding of the unwanted, unbound polymerase complex components to the solid phase support is reversible. In other embodiments, the binding is irreversible. The process is described, for example, with reference to FIGS. 2, 3, 4, and 7.

In some embodiments, the purification moiety and the purification moiety-binding partner are each DNA sequences capable of hybridizing to each other.

In some embodiments, the purification moiety is biotin and the purification moiety-binding partner of the solid phase support is avidin or streptavidin. The avidin-biotin system, and in particular the streptavidin-biotin system, is one of the most widely used affinity bindings in molecular, immunological and cellular assays. In general, a target molecule that is to be isolated from a mixture is bound either directly to biotin or to a biotinylated intermediate. Such intermediate may be almost any molecule or macromolecule that will complex with or conjugate to a target molecule.

In embodiments of the process of positive isolation of the polymerase complex, the target molecule that is bound to biotin or to a biotinylated intermediate is the polymerase complex (FIG. 5). In embodiments of the process of displacement purification, active and inactive polymerase complexes are the targets that are bound to biotin or to a biotinylated (FIG. 4). In embodiments of the process of negative isolation of the polymerase complex, the target molecule that is bound to biotin or to a biotinylated intermediate is any one of the unbound polymerase components e.g. unbound polymerase enzyme, and unbound polymerase-nanopore complexes (FIG. 7). In all embodiments, the biotinylated target is bound to avidin, streptavidin, or analogs and derivatives thereof, which may be bound to a solid phase for ease of isolation.

The high affinity of biotin for streptavidin or avidin provides the basis for many established procedures for the detection and isolation of biotin-associated targets. The binding between avidin and biotin (affinity constant, k approx. 10-15 M) is regarded as one of the strongest non-covalent, biological interactions known. (N. M. Green, Methods Enzymol. 184:51-67, 1990). This strong binding is maintained even when either or both binding partners are bound covalently to other materials. The bond forms very rapidly and is considered to be stable under a wide range of pH, temperature and other denaturing conditions (Savage et al., Avidin-Biotin Chemistry: A Handbook, 1992: 1-23, Rockford, Pierce Chemical Company). Dissociation of biotin from streptavidin is reported to be about 30 times faster than dissociation of biotin from avidin. (Piran &. Riordan. J. Immunol. Methods 133, 141-143, 1990).

Some applications which use the biotin-streptavidin (or avidin) linkage rely on the essentially irreversible binding of the two binding partners. For example, irreversible binding can be utilized in methods of negative isolation, whereby the desired polymerase complex is not bound to a solid phase support, and remains isolated in the fraction that is depleted of unbound polymerase components. In other methods provided herein, the isolation of the desired polymerase complexes relies on the reversible binding of the binding partners, whereby the interaction between the biotinylated purification moiety and the purification moiety-binding partner is released by a displacer ligand. For example, reversible binding can be utilized in methods of positive isolation, whereby the desired polymerase complex is bound to a solid phase support, and is thereby isolated from the unbound polymerase complex components.

In some embodiments, releasable binding of the binding partners can be obtained by using modified biotin and derivatives thereof. For example, in some embodiments, the purification binding moiety is dethiobiotin as the purification moiety, streptavidin as the binding partner, and biotin, which has a higher affinity constant for streptavidin than does dethiobiotin, can be used as the displacer ligand. Examples of suitable displacer ligands include biotin, dethiobiotin, streptavidin, or avidin. Biotin is a preferred displacer ligand. The sample containing the linkage, preferably is an aqueous sample, to which the displacer ligand is added, and the reaction mixture allowed to stand under appropriate conditions for a time interval to allow the displacer ligand to bind, and one or both of the components of the linkage may then be separated. Examples of suitable releasable ligands include dethiobiotin, iminobiotin, and functionalized azo dyes, streptavidin, succinylated avidin, and avidin. Dethiobiotin is preferred. U.S. Pat. No. 5,332,679. Other biotin analogs that can be used as purification binding moieties include biotin sulfone, and biotin derivatives including caproylamidobiotin and biocytin U.S. Pat. Nos. 4,656,252; 4,478,914; and 4,282,287.

In other embodiments, the purification binding moiety is a derivative of desthiobiotin. Modified biotin derivatives are commercially available under the name DSB-X™ Biotin (Molecular Probes, Eugene, Oreg., USA). DSB-X™ biotin is a derivative of desthiobiotin, a stable biotin precursor. DSB-X™ biotin utilizes a seven-atom spacer to increase the ability of the DSB-X™ biotin conjugate to bind in the deep biotin-binding pocket of streptavidin or avidin. The derivative has a moderate affinity for avidin and streptavidin. Their interaction is rapidly reversed by low concentrations of free biotin or desthiobiotin at neutral pH and room temperature. Targets complexed with DSB-X biotin-labeled molecules can be selectively detected with avidin or streptavidin conjugates or isolated on affinity matrices followed release of DSB-X biotin-labeled biomolecules, under gentle conditions (Hirsch et al. Anal. Biochem. 308, 343-357, 2002). DES-X™ biotin can be conjugated to various molecules, with the use of streptavidin or avidin coated solid phase for immobilization of target, or one may use a DES-X™-coated solid phase and streptavidin or avidin labeled molecules. Molecular Probes provides a variety of antibody conjugates of DSB-X™ biotin as well as DSB-X™ biotin agarose.

Releasable streptavidin-biotin or avidin-biotin conjugate can also be obtained, for example, by using chemical cleavable linkers that link the biotin to the binding partner. Shimkus et al (Proc. Natl. Acad. Sci. USA, 82, pp. 2593-2597, 1985) describe the use of a disulfide bond in a linker that joined biotin to C-5 of the pyrimidine ring, as a means for reversibly binding nucleotides to avidin-agarose columns. This principle is also described in U.S. Pat. No. 4,772,691. In other embodiments, linkages that are specifically cleavable by enzymatic or chemical agents can be introduced between the biotin molecule and the binding partner e.g. peptide bonds cleavable by various peptidases, disaccharide linkages cleavable by disaccharidases, or chemical bonds that can be selectively broken under mild reducing, oxidizing, acidic, or basic conditions (U.S. Pat. No. 5,215,927). For example One such linker, Sulfo-NHS-SS-biotin, is commercially available (Pierce Biotechnology Inc, Rockford, Ill. USA). The commercial available CEL-Lection™ Biotin Binder (Dynal Biotech AS, Prod. No. 115.33) contains magnetic beads coated with streptavidin via a DNA linker to provide for cleavable site for target release. The release occurs by incubation with DNAse for 15 minutes at room temperature. Photolabile linkages or photocleavable biotin phosphoramidites (Olejnik et al., Nucleic Acids Res. 24: 361-366, 1996) or the use of polymer conjugates together with streptavidin mutants that yields temperature or pH dependent release can also be used (Ding et al., Bioconjugate Chem. 10: 395-400 [1999]; (Bulmus et al., Bioconjugate Chem. 11:78-83 [2000]). In preferred embodiments, the solid phase comprises magnetic particles and the magnetic particles and attached components or polymerase complexes are isolated from the mixed population of components and complexes by magnetic aggregation.

All parameters involved in the attachment and release system described herein may vary dependent on targets to be isolated, the ligand system used, the modified biotin and the avidin or modified avidin, or streptavidin used, and also the type of solid phase used e.g. size of the magnetic beads. All conditions used may readily be determined by those skilled in the art for any given target and binding pairs used.

In other embodiments, the methods provided herein include the use of monomeric avidin (Pierce Biotechnology Inc., Rockford, Ill. USA.), cleavage of the biotin or streptavidin and the use of biotin analogues like N-hydroxysuccinimide-iminobiotin and amidobiotins. N-hydroxysuccinimide-iminobiotin (NHS-iminobiotin) is a guanido analog of NHS-biotin with a pH sensitive binding affinity for streptavidin.

In some embodiments, the purification moiety-binding partner/ligand is avidin or streptavidin, which can be recombinant or chemically modified, and which can form stable binding to biotin or analogs thereof. For example, publication WO 01/05977 by Kulomaa et al. discloses mutations in both avidin and streptavidin that replace a specific tryptophan residue with lysine to produce stable dimers that exhibit reversible biotin-binding properties. Other modified avidins and streptavidins having reduced affinity for biotin and that can be used as purification moiety-binding partners in the purification methods provided herein are described for example in U.S. Pat. Nos. 6,022,951, 6,391,571; 6,312,916; 6,417,331; 6,165,750 and 6,156,493. Additionally, polypeptides that are substantially immunologically equivalent to natural streptavidin and are able to bind to biotin or biotin derivatives or analogues can also be used as purification moiety-binding partners in the methods provided herein (U.S. Pat. No. 5,168,049).

In some embodiments, the ligand i.e. the purifying moiety binding partner, is an antibody which is directed against the purifying moiety. The antibody may also be directed against another antibody (that is, an anti-antibody) that is linked to the purification moiety. Both monoclonal and polyclonal antibodies can be used, and they can be whole molecules or various fragments thereof. Antibody specific for a particular ligand may be produced by methods well known and documented in the art. Antibodies for use in methods of the present invention may be of any species, class or subtype providing that such antibodies are capable of forming a linkage with a particular binding partner and can be biotinylated with a modified biotin. Thus antibodies for use in the present invention include: any of the various classes or sub-classes of immunoglobulin, e.g. IgG, IgA, IgM, IgD or IgE derived from any animal, intact antibodies or "fragments" of antibodies, monoclonal or polyclonal, chimeric antibodies, or synthetically made or altered antibody-like structures. Also included are functional derivatives or "equivalents" of antibodies e.g. single chain antibodies.

The modified biotin-binding compound (e.g. nitro-streptavidin or avidin), or the modified biotin, if desired, may be covalently attached to a suitable support through reactive groups on the substrate surface by methods well known in the art.

The solid support may be any of the well-known supports or matrices which are currently widely used or proposed for immobilization, separation etc., in chemical or biochemical procedures. These may take the form of particles, sheets, dip-sticks, gels, filters, membranes, microfibre strips, tubes, wells or plates, fibres or capillaries, combs, pipette tips, microarrays or chips or combinations thereof, and conveniently may be made of a polymeric material, e.g. agarose, Sepharose, cellulose, nitrocellulose, alginate, Teflon, latex, acrylamide, nylon membranes, plastic, polystyrene, glass or silica or metals. Numerous suitable solid supports are commercially available. Preferred solid supports are materials presenting a high surface area for binding of the modified biotin or modified biotin-binding compound. Such supports will generally have an irregular surface and may for example be porous or particulate, e.g. particles, fibers, webs, sinters or sieves. Particulate materials e.g. beads are generally preferred due to their greater binding capacity, particularly polymeric beads/particles.

In some embodiments, a particulate solid support used according to the methods provided herein comprise spherical beads. The size of the beads is not critical, but they may for example be of the order of diameter of at least 0.01 μm, and have a maximum diameter of preferably not more than 10 and more preferably not more than 6 μm. For example, beads of diameter 1.0 μm, 2.8 μm and 4.5 μm have been shown to work well. Monodisperse particles, that is those which are substantially uniform in size (e.g. size having a diameter standard deviation of less than 5%) have the advantage that they provide very uniform reproducibility of reaction. Monodisperse polymer particles produced by the technique described in U.S. Pat. No. 4,336,173 are also suitable.

Non-magnetic polymer beads suitable for use in the method of the invention are available from Dynal Biotech AS (Oslo, Norway) under the trademark DYNOSPHERES, as well as from Qiagen, GE Healthcare Life Sciences, Serotec, Seradyne, Merck, Nippon Paint, Chemagen, Promega, Prolabo, Polysciences, Agowa and Bangs Laboratories.

However, to aid manipulation and separation of immobilized material, and also to facilitate automation if required, magnetizable ("magnetic") beads are preferred. The term "magnetic" as used herein means that the support is capable of having a magnetic moment imparted to it when placed in a magnetic field, and thus is displaceable under the action of that field. In other words, a support comprising magnetic particles may readily be removed from other components of a sample by magnetic aggregation, which provides a quick, simple and efficient way of separating the particles following the binding of any modified biotin or modified biotinylated moieties.

Thus, the magnetic particles with the modified biotin or modified biotinylated moieties attached via conjugation to a modified biotin-binding compound, e.g. nitro-streptavidin (avidin), may be removed onto a suitable surface by application of a magnetic field, e.g. using a permanent magnet. It is usually sufficient to apply a magnet to the side of the vessel containing the sample mixture to aggregate the particles to the wall of the vessel and to remove the remainder of the sample so that the remaining sample and/or the particles are available for any desired further steps. The well-known monodisperse polymeric superparamagnetic beads sold by Dynal Biotech AS (Oslo, Norway) under the trade mark DYNABEADS, are exemplary of commercially available magnetic particles which may be used or modified for use according to the invention.

Enzymes of Enzyme-Polymer Complexes and Enzyme-Nanopore Complexes:

The enzymes of the polymerase complexes and of the nanopore sequencing complexes include polynucleotide processing enzymes, e.g. DNA and RNA polymerases, and reverse transcriptases. The enzyme of the polymerase complexes and of the nanopore sequencing complexes can be a wild-type enzyme, or it can be a variant form of the wild-type enzyme. Variant enzymes can be engineered to possess characteristics that are altered relative to those of the parent enzyme. In some embodiments, the enzyme of the enzyme-polymer complex that is altered is a polymerase. The altered characteristics of the polymerase enzyme include changes in enzyme activity, fidelity, processivity, elongation rate, stability, or solubility. The polymerase can be mutated to reduce the rate at which the polymerase incorporates a nucleotide into a nucleic acid strand (e.g., a growing nucleic acid strand). The reduced velocities (and improved sensitivities) can be achieved by a combination of site-specific mutagenesis of the nanopore protein and the incorporation of DNA processing enzymes e.g. DNA polymerase, into the nanopore.

Examples of DNA polymerase enzymes that can be complexed with template substrates in polymerase complexes and/or nanopore sequencing complexes include without limitation wild type or variants of Pol6 DNA polymerase from *Clostridium* phage phiCPV4 (GenBank Accession No.: AFH27113.1, and the *Bacillus subtilis* bacteriophage DNA polymerase Phi29 (Genbank Accession No. X53371). The wild type and variant polymerase preferably display at least one of the altered characteristics disclosed herein.

In some cases, the rate at which a nucleotide is incorporated into a nucleic acid strand can be reduced by functionalizing the nucleotide and/or template strand to provide steric hindrance, such as, for example, through methylation of the template nucleic acid strand. In some instances, the rate is reduced by incorporating methylated nucleotides.

The enzymes of the polymerase complexes and of the nanopore sequencing complexes may be modified to comprise one or more attachment components and/or attachment sites that serve to link the enzyme of the polymerase complex to the nanopore that is inserted into the membrane of a biochip. Alternatively, enzymes of the polymerase complexes and of the nanopore sequencing complexes may be modified to comprise one or more attachment components and/or attachment sites that serve to link the enzyme of the polymerase complex to a nanopore to form a nanopore sequencing complex that is inserted into the membrane of a biochip. Similarly, the nanopore of the polymerase complex and/or of the nanopores sequencing complex may also be modified to comprise one or more attachment components and/or attachment sites to link the nanopore to the enzyme-polymer complex.

Nanopores:

The nanopores of the nanopore sequencing complex include without limitation biological nanopores, solid state nanopores, and hybrid biological-solid state nanopores. Biological nanopores of the nanopore sequencing complexes include OmpG from *E. coli*, sp., *Salmonella* sp., *Shigella* sp., and *Pseudomonas* sp., and alpha hemolysin from *S. aureus* sp., MspA from *M. smegmatis* sp. The nanopores may be wild-type nanopores, variant nanopores, or modified variant nanopores.

Variant nanopores can be engineered to possess characteristics that are altered relative to those of the parent enzyme. In some embodiments, the variant nanopore of the nanopore sequencing complex is engineered to reduce the ionic current noise of the parental nanopore from which it is derived. An example of a variant nanopore having an altered characteristic is the OmpG nanopore having one or more mutations at the constriction site, which decrease the ionic noise level relative to that of the parent OmpG. The reduced ionic current noise provides for the use of these OmpG nanopore variants in single molecule sensing of polynucleotides and proteins. In other embodiments, the variant OmpG polypeptide can be further mutated to bind molecular adapters, which while resident in the pore slow the movement of analytes, e.g., nucleotide bases, through the pore and consequently improve the accuracy of the identification of the analyte (Astier et al., J Am Chem Soc 10.1021/ja057123+, published online on Dec. 30, 2005).

Modified variant nanopores are typically multimeric nanopores whose subunits have been engineered to affect inter-subunit interaction. Altered subunit interactions can be exploited to specify the sequence and order with which monomers oligomerize to form the multimeric nanopore in a lipid bilayer. This technique provides control of the stoichiometry of the subunits that form the nanopore. An example of a multimeric nanopore whose subunits can be modified to determine the sequence of interaction of subunits during oligomerization is an OIL nanopore, Linking Nanopore to Polymerase:

The polymerase complex e.g. polymerase-polynucleotide complex, can be attached to the nanopore in any suitable way. Attaching polymerase complexes to nanopores may be achieved using the SpyTag/SpyCatcher peptide system (Zakeri et al. PNAS109:E690-E697 [2012]) native chemical ligation (Thapa et al., Molecules 19:14461-14483 [2014]), sortase system_(Wu and Guo, Carbohydr Chem 31:48-66 [2012]; Heck et al., Appl Microbiol Biotechnol 97:461-475 [2013]), transglutaminase systems (Dennler et al., Bioconjug Chem 25:569-578 ['2014]), formylglycine linkage (Rashidian et al., Bioconjug Chem 24:1277-1294 [2013]), or other chemical ligation techniques known in the art.

In some instances, the polymerase is linked to the nanopore using Solulink™ chemistry. Solulink™ can be a reaction between HyNic (6-hydrazino-nicotinic acid, an aromatic hydrazine) and 4FB (4-formylbenzoate, an aromatic aldehyde). In some instances, the polymerase is linked to the nanopore using Click chemistry (available from LifeTechnologies, for example).

In some cases, zinc finger mutations are introduced into a nanopore e.g. an a-hemolysin molecule and then a molecule is used (e.g., a DNA intermediate molecule) to link the polymerase to the zinc finger sites on the hemolysin.

Additionally, polymerase complexes can be attached to a nanopore e.g. aHL, OmpG, by means of a linker molecule that is attached to a nanopore at an attachment site. In some cases, the polymerase-DNA complex is attached to the nanopore with molecular staples. In some instances, molecular staples comprise three amino acid sequences (denoted linkers A, B and C). Linker A can extend from a nanopore monomer, Linker B can extend from the polymerase of the polymerase-DNA complex, and Linker C then can bind Linkers A and B (e.g., by wrapping around both Linkers A and B) and thus the polymerase of the polymerase-DNA complex to the nanopore. Linker C can also be constructed to be part of Linker A or Linker B, thus reducing the number of linker molecules.

Other linkers that may find use in attaching the polymerase to a nanopore are direct genetic linkage (e.g., $(GGGGS)_{1-3}$ amino acid linker (SEQ ID NO: 1)), transglutaminase mediated linking (e.g., RSKLG (SEQ ID NO: 2)), sortase mediated linking, and chemical linking through cysteine modifications. Specific linkers contemplated as useful herein are $(GGGGS)_{1-3}$ (SEQ ID NO: 1), K-tag (RSKLG (SEQ ID NO: 2)) on N-terminus, ΔTEV site (12-25), ΔTEV site+N-terminus of SpyCatcher (12-49).

An exemplary method for attaching a polymerase complex to a nanopore in a membrane involves attaching a linker molecule to a nanopore or mutating a nanopore to have an attachment site and then attaching a polymerase-polynucleotide complex to the attachment site or attachment linker. The polymerase-polynucleotide complex is attached to the attachment site or attachment linker after the nanopore is inserted in the membrane. In some cases, a polymerase-polynucleotide complex is attached to each of a plurality of nanopores that are inserted into a membrane and disposed over wells and/or electrodes of a biochip.

In some instances, the enzyme of the enzyme-polymer complex is expressed as a fusion protein that comprises a linker peptide. In some embodiments, a polymerase is the enzyme of the enzyme-polymer complex, and a polynucleotide is the polymer. The polymerase of the polymerase-polynucleotide complex is expressed as a fusion protein that comprises a SpyCatcher polypeptide, which can be covalently bound to a nanopore that comprises a SpyTag peptide (Zakeri et al. PNAS109:E690-E697 [2012]).

Polymerase complexes may be attached to nanopores using methods described, for example, in PCT/US2013/068967 (published as WO2014/074727; Genia Technologies, Inc.), PCT/US2005/009702 (published as WO2006/028508; President and Fellows of Harvard College), and PCT/US2011/065640 (published as WO2012/083249; Columbia University).

Stoichiometries:

The enzymes of the polymerase complex e.g. a DNA polymerase, may be modified to comprise one or more attachment components and/or attachment sites that serve to link the enzyme-polymer complex to the nanopore inserted into the membrane. Similarly, the nanopore to which the polymerase complex is attached may also be modified to comprise one or more attachment components and/or attachment sites to link the nanopore to the polymerase complex.

In some embodiments, a single polymerase complex is attached to the nanopore in the membrane. In other embodiments, two or more polymerase complexes are attached to the nanopore in the membrane. The single polymerase complex may be attached to the nanopore at one or more attachment sites present on the nanopore protein. In some embodiments, one or more polymerase complexes are attached to a monomeric nanopore protein e.g. an OmpG nanopore. In other embodiments, one or more polymerase complexes are attached to a multimeric nanopore protein that comprises at least two nanopore subunits e.g. heptameric aHL nanopore. A polymerase complex can be attached to an attachment site on a single subunit of a multimeric nanopore. Alternatively, the polymerase complex may be attached to the multimeric nanopore at two or more attachments sites present on each of two or more subunits of a multimeric nanopore.

Polymerase complexes may be attached to one or more subunits of homo-oligomeric or of hetero-oligomeric nanopores. For example, a polymerase complex may be coupled to an aHL nanopore consisting of 7 identical subunits, which may be wild-type, variants, or modified variants. Alternatively, the polymerase complex may be coupled to an aHL nanopore consisting of at least two different subunits, of which one or more may be modified.

Oligomeric nanopores e.g. a-HL, are proteins that can self-assemble from subunits that are monomers, concatemers of monomers, or a combination of monomers and concatemers of monomers. Subunits that are concatemers of monomers can comprise two, three or more monomers that are linked to each other by a linker or that are each encoded by a single polynucleotide as a fusion protein. Accordingly, the polymerase complex may be attached to a monomer subunit, or to a concatamer of monomer subunits of an oligomeric nanopore. In some embodiments, the polymerase complex is a DNA polymerase-DNA template complex that is attached to a monomeric nanopore e.g. an OmpG, which may be wild type, or a variant having altered characteristics. In other embodiments, the polymerase complex is a DNA polymerase-DNA template complex that is attached to an oligomeric nanopore, which can be a homo-oligomeric or a hetero-oligomeric nanopore e.g. an OIL nanopore, which may be wild-type, a variant, or a modified variant nanopore.

Forming Bilayers on Biochips:

Methods for creating lipid bilayers comprising nanopores in a biochip are described at least at paragraphs [00131]-[00196] in PCT/US2014/061854 (published as WO2015/061511, Genia Technologies, Inc.). A lipid bilayer can be created on top of each one of multiple electrodes that make up an array of individually controlled electrodes and a single nanopore can be inserted into each bilayer atop each electrode in an array of individually controlled electrodes, In some embodiments, sequencing nanopore complexes are formed on a semiconductor chip having multiple electrodes, to which a lipid solution is applied to create a lipid bilayer. The lipid solution may be a solution of an organic solvent e.g. decane, hexane, tridecane etc., and lipid molecules, such as diphytanoylphosphatidylcholine (DPhPC), 1,2-diphytanoyi-sn-glycero-3-phosphocholine, Lysophosphatidylcholine (LPC), 1,2-Di-O-Phytanyl-sn-Glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy(polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy(polyethylene glycol)-2000]; 1,2-dioleoyl-sn-glycero-3-phosphoethanolamine-N-lactosyl; GM1 Ganglioside, or any combination thereof. Methods for applying the lipid solution and forming the lipid bilayer is described at least at paragraphs [00148] to [00152] of WO2015/061510.

Inserting a Nanopore:

In some instances, a nanopore is inserted in the membrane (e.g., by electroporation). Methods for inserting a nanopore in a membrane are provided at least at paragraphs [00197]-[00203] of WO2015/061510. The nanopore can be inserted by a stimulus signal such as electrical stimulus, pressure stimulus, liquid flow stimulus, gas bubble stimulus, sonication, sound, vibration, or any combination thereof.

In some embodiments, inserting the nanopore comprises applying a stimulus electroporation pulse) through the electrode(s) to facilitate the insertion of said nanopore. In some cases, this is followed by a second electrical detection pulse to detect the insertion of said nanopore in said lipid bilayer. In some cases, the application of a stimulus voltage and subsequent detection voltage is repeated with the stimulus voltage gradually increasing in magnitude until a pore is detected during a detection pulse. The electrode is then disabled and no further pulses are applied. In other embodiments, the nanopore inserts itself into the membrane.

Nanopores of the nanopore sequencing complexes described herein may be inserted in a membrane, e.g. a lipid bilayer, and disposed adjacent or in proximity to a sensing electrode of a sensing circuit, such as an integrated circuit of a nanopore based sensor e.g. a biochip. The nanopore may be inserted in a membrane and disposed of a well and/or sensing electrodes in the biochip. Multiple nanopore sensors may be provided as arrays. Biochips and methods for making biochips are described in PCT/US2014/061854 (published as WO2015/061511, Genia Technologies, Inc.), which is herein incorporated by reference in its entirety Methods for Sequencing:

The molecules being characterized using the nanopores of the nanopore sequencing complexes described herein can be of various types, including charged or polar molecules such as charged or polar polymeric molecules. Specific examples include ribonucleic acid (RNA) and deoxyribonucleic acid (DNA) molecules. The DNA can be a single-strand DNA (ssDNA) or a double-strand DNA (dsDNA) molecule.

In one aspect, provided are methods for sequencing nucleic acids using the nanopore sequencing complexes described herein. In some embodiments, the methods comprise isolating a polymerase complex from a mixture of polymerase complex components according to any one of the methods described herein, and attaching the isolated polymerase complex to a nanopore inserted in a lipid membrane of a biochip. In other embodiments, the sequencing methods comprise isolating a nanopore sequencing complex from a mixture of complex components, and inserting the isolated nanopore sequencing complex into a lipid membrane of a biochip. The nanopore sequencing complexes prepared as described herein can be used for determining the sequence of nucleic acids according to other nanopore sequencing platforms known in the art that utilize enzymes in the sequencing of polynucleotides. For example, nanopore sequencing complexes can be prepared according to the method described herein for sequencing nucleic acids according to the helicase and exonuclease-based methods of Oxford Nanopore (Oxford, UK), Illumina (San Diego, Calif.), and the nanopore sequencing-by-expansion of Stratos Genomics (Seattle, Wash.).

In some embodiments, sequencing of nucleic acids comprises preparing nanopore sequencing complexes as described herein, and determining polynucleotide sequences using tagged nucleotides as is described in PCT/US2013/068967 (entitled "Nucleic Acid Sequencing Using Tags" filed on Nov. 7, 2013, which is herein incorporated by reference in its entirety). For example, a nanopore sequencing complex that is situated in a membrane (e.g., a lipid bilayer) adjacent to or in sensing proximity to one or more sensing electrodes, can detect the incorporation of a tagged nucleotide by a polymerase as the nucleotide base is incorporated into a strand that is complementary to that of the polynucleotide associated with the polymerase, and the tag of the nucleotide is detected by the nanopore. The polymerase-polynucleotide complex can be associated with the nanopore as described above.

Tags of the tagged nucleotides can include chemical groups or molecules that are capable of being detected by a nanopore. Examples of tags used to provide tagged nucleotides are described at least at paragraphs [0414] to [0452] of PCT/US2013/068967. Nucleotides may be incorporated from a mixture of different nucleotides, e.g., a mixture of tagged dNTPs where N is adenosine (A), cytidine (C), thymidine (T), guanosine (G) or uracil (U). Alternatively, nucleotides can be incorporated from alternating solutions of individual tagged dNTPs, i.e., tagged dATP followed by tagged dCTP, followed by tagged dGTP, etc. Determination of a polynucleotide sequence can occur as the nanopore detects the tags as they flow through or are adjacent to the nanopore, as the tags reside in the nanopore and/or as the tags are presented to the nanopore. The tag of each tagged nucleotide can be coupled to the nucleotide base at any position including, but not limited to a phosphate (e.g., gamma phosphate), sugar or nitrogenous base moiety of the nucleotide. In some cases, tags are detected while tags are associated with a polymerase during the incorporation of nucleotide tags. The tag may continue to be detected until the tag translocates through the nanopore after nucleotide incorporation and subsequent cleavage and/or release of the tag. In some cases, nucleotide incorporation events release tags from the tagged nucleotides, and the tags pass through a nanopore and are detected. The tag can be released by the polymerase, or cleaved/released in any suitable manner including without limitation cleavage by an enzyme located near the polymerase. In this way, the incorporated base may be identified (i.e., A, C, G, T or U) because a unique tag is released from each type of nucleotide (i.e., adenine, cytosine, guanine, thymine or uracil). In some situations, nucleotide incorporation events do not release tags. In such a case, a tag coupled to an incorporated nucleotide is detected with the aid of a nanopore. In some examples, the tag can move through or in proximity to the nanopore and be detected with the aid of the nanopore.

In some cases, tagged nucleotides that are not incorporated pass through the nanopore. The method can distinguish between tags associated with un-incorporated nucleotides and tags associated with incorporated nucleotides based on the length of time the tagged nucleotide is detected by the nanopore. In one embodiment, an un-incorporated nucleotide is detected by the nanopore for less than about 1 millisecond and an incorporated nucleotide is detected by the nanopore for at least about 1 millisecond.

Thus, in one aspect, the disclosure provides for a method for sequencing a polynucleotide from a biological sample, with the aid of a nanopore sequencing complex. The sample polynucleotide is combined with a polymerase, to provide the enzyme-polymer complex portion of the nanopore sequencing complex. In one embodiment, the sample polynucleotide is a sample ssDNA strand, which is combined with a DNA polymerase to provide a DNA polymerase-DNA complex. The DNA polymerase-sample ssDNA strand is subsequently attached to a nanopore that has been inserted into a membrane e.g. a lipid bilayer, to provide the nanopore sequencing complex. The nanopore portion of the sequencing complex is positioned in the membrane adjacent to or in proximity of a sensing electrode, as described elsewhere herein. The resulting nanopore sequencing complex is capable of determining the sequence of nucleotide bases of the sample DNA as described elsewhere herein. In other embodiments, the nanopore sequencing complex determines the sequence of double stranded DNA. In yet other embodiments, nanopore sequencing complex determines the sequence of RNA.

In one embodiment, the method provides for sequencing a sample polynucleotide with the aid of a nanopore sequencing complex adjacent to a sensing electrode, and comprises (a) preparing a nanopore sequencing complex by isolating a polymerase complex and attaching the polymerase complex to a nanopore inserted in a lipid membrane of a biochip. Alternatively, the method comprises isolating a nanopore sequencing complex from a mixture of complex components, and inserting the nanopore sequencing complex in the lipid membrane of a biochip. The method further comprises (b) providing tagged nucleotides into a reaction chamber comprising the nanopore sequencing complex, wherein an individual tagged nucleotide of the tagged nucleotides contains a tag coupled to a nucleotide, which tag is detectable with the aid of the nanopore; (c) carrying out a polymerization reaction, with the aid of the polymerase, thereby incorporating an individual tagged nucleotide of the tagged nucleotides into a growing strand complementary to the single stranded nucleic acid molecule from the nucleic acid sample; and (d) detecting, with the aid of the nanopore, a tag associated with the individual tagged nucleotide during and/or upon incorporation of the individual tagged nucleotide, wherein the tag is detected with the aid of the nanopore when the nucleotide is associated with the polymerase. Other embodiments of the sequencing method that comprise the use of tagged nucleotides with the present nanopore sequencing complexes for sequencing polynucleotides are provided in WO2014/074727, which is incorporated herein by reference in its entirety.

Sequencing nucleic acids using AC waveforms and tagged nucleotides is described in US Patent Publication US2014/0134616 entitled "Nucleic Acid Sequencing Using Tags", filed on Nov. 6, 2013, which is herein incorporated by reference in its entirety. In addition to the tagged nucleotides described in US2014/0134616, sequencing can be performed using nucleotide analogs that lack a sugar or acyclic moiety, e.g. (S)-Glycerol nucleoside triphosphates (gNTPs) of the five common nucleobases: adenine, cytosine, guanine, uracil, and thymidine (Horhota et al. Organic Letters, 8:5345-5347 [2006]).

Nucleic Acid Adaptor for Isolating Active Polymerase Complexes:

As mentioned above, also disclosed is a nucleic acid adaptor for isolating active polymerase complexes, polymerase complexes comprising the nucleic acid adaptor, and methods for isolating active polymerase complexes using the nucleic acid adaptor. The isolated polymerase complexes are subsequently incorporated into membranes of biochips to enable nanopore sequencing of polynucleotides.

Aspects discussed herein above with respect to other methods and embodiments of the present disclosure are also applicable with regard to the nucleic acid adaptor for isolating active polymerase complexes, the polymerase complexes comprising the nucleic acid adaptor, the methods for isolating active polymerase complexes using the nucleic acid adaptor, and other methods discussed herein that are enabled by the use of the nucleic acid adaptor. Therefore, such aspects are not being restated in this section, but one of ordinary skill in the art can readily understand that such previously discussed aspects and embodiments can relate to the nucleic acid adaptor and its related methods.

Active Fraction Enrichment via Biotin Labeling and Streptavidin Bead Capture:

Provided below is a description of various aspects of an embodiment of the nucleic acid adaptor of the present disclosure, particularly as it pertains to active fraction enrichment via biotin labeling and streptavidin bead capture.

In one embodiment, the adaptor contains a runway section (sequence) composed of 3 of the 4 nucleotides. This runway section can be 2 to 50 bases long, preferably 8 to 12 bases.

In a more particular embodiment of the adaptor, one of the runway bases may be present 4 to 6 times or a large percentage of the bases. Conversely, one of the bases in the runway could be very sparse (e.g., 1 to 2 bases).

The adaptor and runway sequence are ligated to sample DNA or RNA and form part of the pore/polymerase/sample DNA or polymerase/DNA complex.

To enrich for functional (active) polymerase complexes, a mixture of appropriate buffer, salt, nucleotides (i.e., 3 of 4 nucleotide bases that are complementary to the 3 of 4 nucleotides of the runway sequence), and required divalent metal for enzymatic activity is used to enable the extension of new nucleotide strands comprising the 3 of 4 nucleotide bases complementary to the 3 of 4 nucleotides of the runway sequence. One or more of the 3 nucleotides in the mixture can have a capture moiety attached to the base or position on the base that will not interfere with this biotin. The capture moiety can be any molecule with an affinity for another molecule. As indicated above, the adaptor includes a stop region after the runway sequence. The stop region comprises the nucleotide base (e.g., cytosine) that is not included as one of the three nucleotide bases (e.g., thymine, guanine, adenine) making up the runway sequence and that is not complementary to any of the 3 of 4 nucleotide bases in the mixture. Once the active polymerase reaches the end of the runway sequence, it then encounters the stop region, at which point the polymerase must stop because of a lack of an appropriate nucleotide needed for extend the strand.

The active enzyme ternary complexes extend a new copy strand and incorporate the biotin labeled nucleotides. When the enzyme reaches the position on the runway where no matching nucleotides are present in the mix, it stops. The ternary complex or polymerase/DNA has been labeled.

The biotin labeled complexes represent those complexes that have an active polymerase. Non-active polymerase complexes are not labeled.

A bead or solid surface support functionalized or attached to a molecule or molecules that have an affinity for the labeling moiety are added to the mix and labeled molecules are attracted and caught by the bead/solid support. Unlabeled, inactive complex is washed away and the remaining, active complex is eluted from the bead/solid support and run on the chip. Alternately, the active complex can stay attached to the bead or solid support and then run on the chip.

The result is the sample complex mix; pore/polymerase/template DNA/primer or polymerase/template/primer has been enriched for active polymerase versions of the above complexes.

Figure 15:
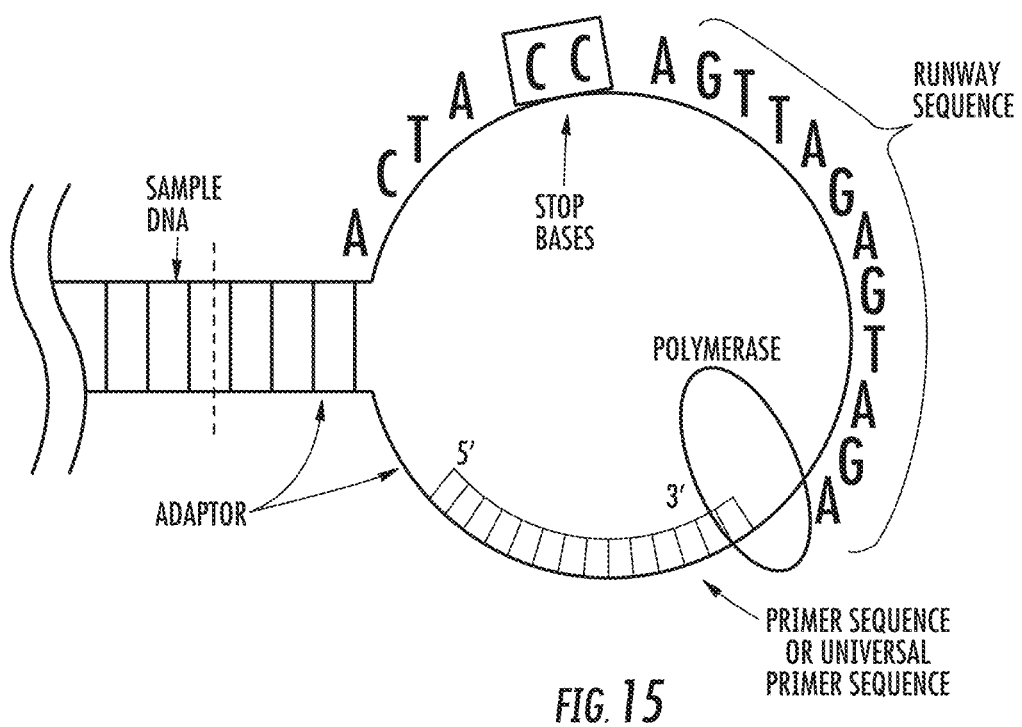
FIG. 15 illustrates one embodiment of a nucleic acid adaptor provided herein for isolating active polymerase complexes. As illustrated, the adaptor is ligated to a sample DNA. The adaptor is also shown to have primer annealed to the primer recognition sequence of the adaptor and a polymerase enzyme associated with the adaptor prior to primer extension. Figure discloses SEQ ID NO: 3.

The schematic shown in FIG. 15 illustrates one embodiment of a nucleic acid adaptor provided herein for isolating active polymerase complexes. As illustrated, the adaptor is ligated to a sample DNA. The adaptor is also shown to have primer annealed to the primer recognition sequence of the adaptor and a polymerase enzyme associated with the adaptor prior to primer extension. As illustrated, the runway sequence is 12 nucleotide bases in length and includes only adenine (A), guanine (G), and thymine (T) nucleotide bases, while the stop region includes only two cytosine (C) nucleotide bases.

Figure 16:
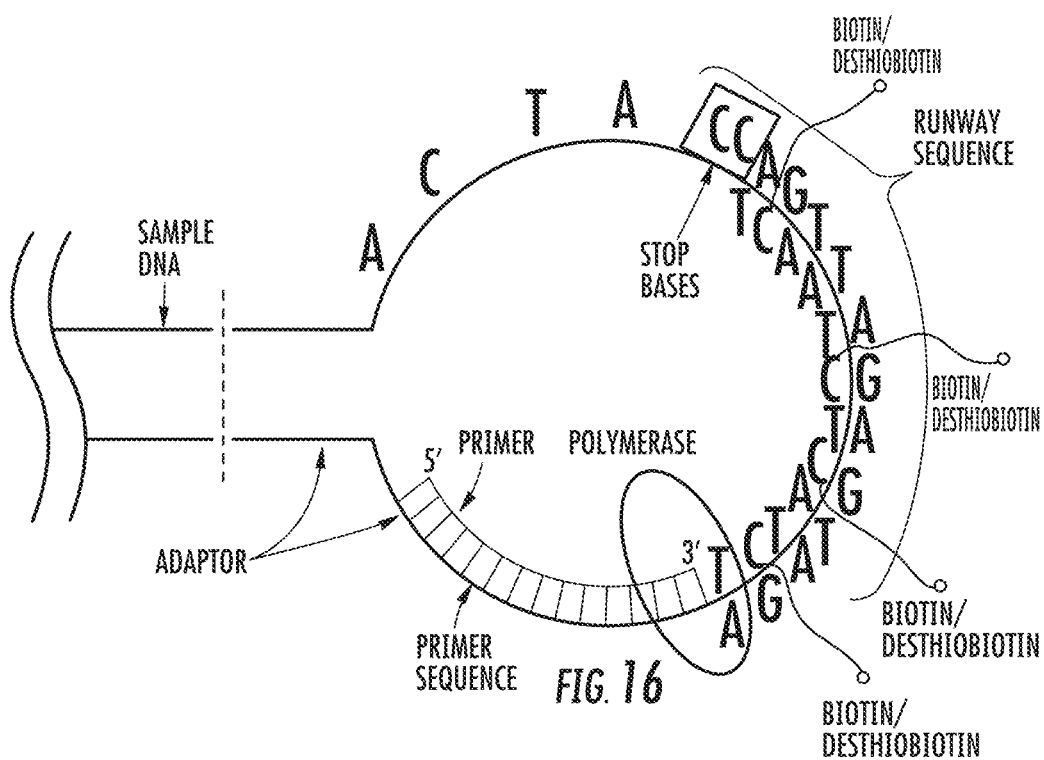
FIG. 16 illustrates one embodiment of a nucleic acid adaptor provided herein for isolating active polymerase complexes. As illustrated, the adaptor is ligated to a sample DNA. The adaptor is also shown to have primer annealed to the primer recognition sequence of the adaptor and an extended sequence complementary to the runway sequence. Also shown is a polymerase enzyme associated with the adaptor. Figure discloses SEQ ID NOS 3 and 4, respectively, in order of appearance.

The schematic shown in FIG. 16 illustrates the same nucleic acid adaptor as shown in FIG. 15. However, as illustrated in FIG. 16, the adaptor is also shown to have a primer annealed to the primer recognition sequence of the adaptor and an extended sequence complementary to the runway sequence. The extended sequence is 12 nucleotide bases in length and includes only adenine (A), cytosine (C), and thymine (T) nucleotide bases. Also shown is a polymerase enzyme associated with the adaptor. Further, the cytosine (C) nucleotide bases of the extended sequence also includes biotin or desthiobiotin moieties.

Below is an example of the reagent mixture added to promote extension of the primer using the adaptor having the runway sequence shown in FIGS. 15 and 16, as follows:

Reagent Mixture:

| | |
|---|---|
| Reagent mix added to promote extension | dTTP<br>dATP<br>biotin - dCTP or desthio-biotin-dCTP<br>MgCl$_2$ or other catalyitic metal<br>HEPES buffer<br>Low [ ] of salt (monovalent salt)<br>Mix is missing dGTP so that extension of nucleic acid strand will stop at C position on adaptor<br>The mix may contain some proportion of non-biotinylated or non-desthiobiotinylated dCTP so that not every "G" position on the template is covered with labeled dCTP.<br>it is also noted that labeled nucleotides can be removed/washed away from the active template complex while the complex is associated with the solid phase, prior to adding the 4th nucleotide during sequencing. |

This method is simple and by optimizing bead binding capacity and labeled dCTP and template concentrations effective enrichment and application to the chip or membrane can be attained.

Once the enriched complex is loaded to the chip and pore/polymerase/template DNA/primer complex is set up over the electrode/wells, the remaining complex and reagents are washed from the chip and replaced with a full set of nucleotide tags and the necessary reagents to perform sequencing by synthesis with Genia nucleotide tags.

Analysis of the resulting sequence is made easier as an anticipated start site at the stop bases can be predicted.

When the polymerase has extended complementary sequence around the entire circular template it will return to the primer and displace it as it continues synthesis. The biotin or desthio-biotin labeled bases are also displaced and are not part of the 2nd or subsequent passes around the template DNA or RNA.

The biotin or desthiobiotin labeling/enrichment can also be performed on linear templates.

Figure 17:
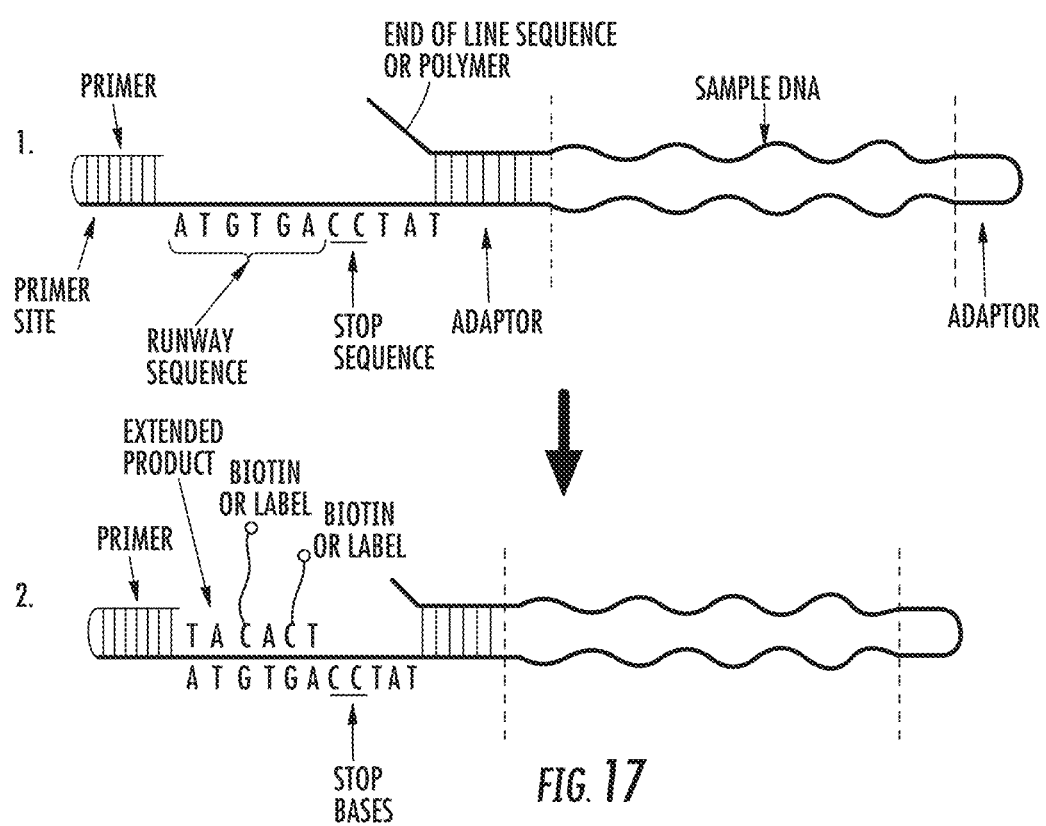
FIG. 17 illustrates one embodiment of a nucleic acid adaptor provided herein for isolating active polymerase complexes. As illustrated, the adaptor is ligated to a sample DNA. The adaptor is linear and is also shown to have primer annealed to the primer recognition sequence of the adaptor. Embodiment (1) illustrates the adaptor before enrichment extension of the runway sequence. Embodiment (2) illustrates the adaptor after enrichment extension of the runway sequence. Figure discloses SEQ ID NOS 5 and 5, respectively, in order of appearance.

The schematic shown in FIG. 17 illustrates one embodiment of a nucleic acid adaptor provided herein for isolating active polymerase complexes. As illustrated, the adaptor is ligated to a sample DNA. The adaptor is linear and is also shown to have primer annealed to the primer recognition sequence of the adaptor. Embodiment (1) illustrates the adaptor before enrichment extension of the runway sequence. Embodiment (2) illustrates the adaptor after enrichment extension of the runway sequence. Those linear samples with no extended product on the runway will not be labeled and subsequently will be washed away in enrichment.

EXAMPLES

Example 1

Displacement Purification—Isolation of Active Polymerase Complexes

This example relates to a method for purifying an active polymerase-template complex. The active complex comprises an active polymerase, which is associated with a self-primed DNA template. A circular DNA can also be used in the presence of an oligonucleotide primer that can be extended in subsequent nanopore sequencing of the template.

According to the method, the active complex was purified from inactive complexes by virtue of the activity of the polymerase as described elsewhere herein.

Ternary complexes were prepared by incubating self-priming DNA templates, polymerase, and biotinylated capture oligonucleotides in a first reaction mixture (I). In cases where a circular DNA template is used, a primer oligonucleotide is included as a component of the ternary complex. Monomeric avidin magnetic beads (BcMag™ from Bioclone Inc. San Diego, Calif.) were prepared according to the manufacturer's instructions by treating the beads with 1 mg/ml BSA, then removing excess BSA by washing the beads with wash buffer 75 mM KGlu, 20 mM HEPES, 3 mM CaCl2), 1 mM TCEP, 0.01% tween20, pH 8.0. Details for conditioning the avidin beads are provided by the manufacturer at www.bioclone.us/files/BcMag_Monomer_Avidin_Magnetic_Beads.pdf.

Two hundred microliters of reaction mixture (1) comprising ternary complexes were incubated with the prepared beads for 30 minutes at room temperature. The reaction mixture (1) was placed on a magnetic separator, and the supernatant containing unbound complex components was removed.

The ternary complexes bound to the beads were washed then resuspended with extension buffer 75 mM KGlu, 20 mM HEPES, 10 mM MgCl2, 150 uM dNTP, 1 mM TCEP, 0.01% tween20, pH 8.0 for 5 minutes at room temperature to allow for extension of the self-primed template. The beads were placed on a magnetic separator, and the supernatant was collected, as complexes comprising active polymerase would be dissociated from the capture oligonucleotide.

Figure 8:
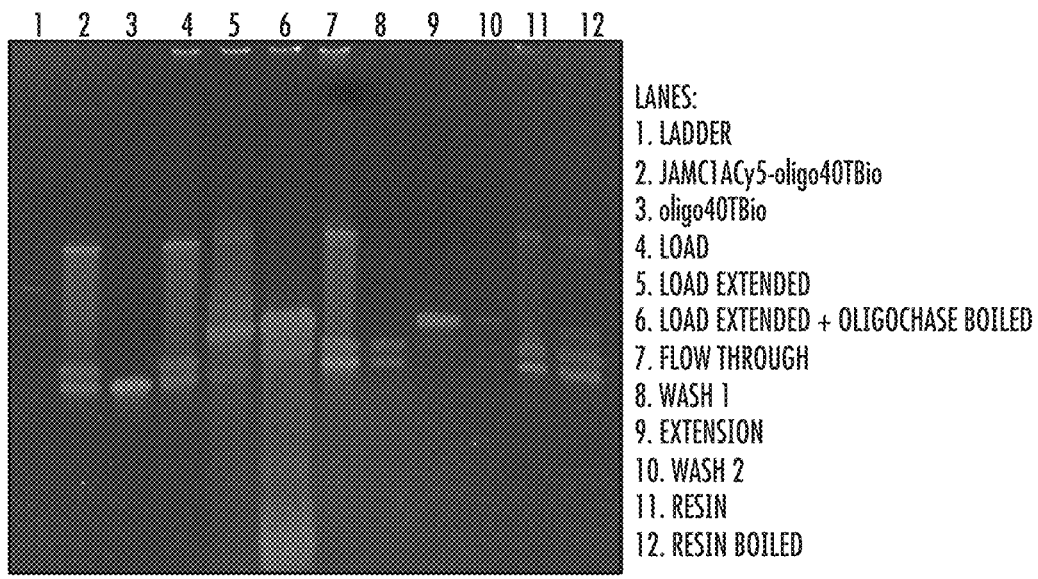
FIG. 8 illustrates a urea gel of various fractions in the isolation process of active polymerase complexes. Reference is made to Example 1.

Purification of the active polymerase complex was visualized using a urea-TBE gel stained with SYBR gold stain (FIG. 8). Lane 1 shows the molecular weight markers. Lane 2 shows the self-priming template coupled with biotinylated capture oligonucleotide. Lane 3 shows the biotinylated capture oligonucleotide alone. Lane 7 shows the unbound fraction. Lane 8 shows the fraction following the first wash of the beads. Lane 9 shows the fraction containing the purified active polymerase complex having the extended DNA template containing the active polymerase complex. Lane 10 shows the fraction from the second wash. Lanes 11 and 12 show that unextended DNA templates complexed with the biotinylated oligonucleotide remained bound to the avidin beads. Lane 12 shows that in this experiment, some of the active polymerase and associated extended DNA template had not been eluted from the beads.

These data show that active polymerase complexes can be isolated according to the displacement purification method described herein.

Example 2

Positive Enrichment—Isolation of Polymerase Complexes

This example relates to a method for purifying a sequencing complex comprising a nanopore attached to a polymerase, which in turn is associated to a polynucleotide template. In the positive enrichment method the affinity purification is of active nanopore-polymerase-template complexes.

A schematic of the process is provided in FIGS. 5 and 6.

Figure 9:
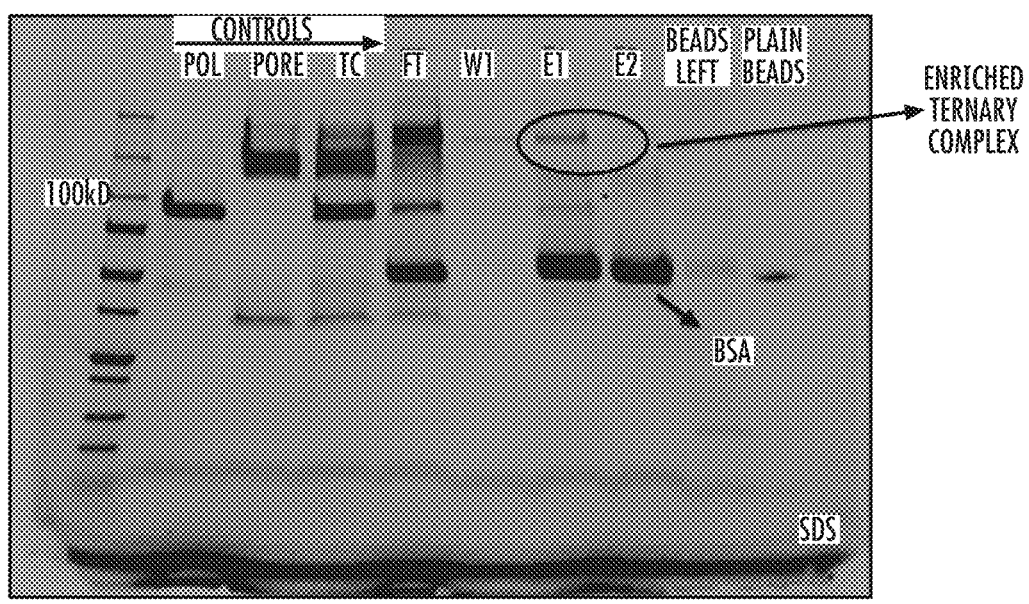
FIG. 9 illustrates a urea gel of various fractions in the process for positively isolating a polymerase complex. Reference is made to Example 2.

Briefly, self-priming hairpin DNA template was annealed to a desthiobiotinylated (DES) primer having a TEG linker according to the manufacturer's instructions. The DES primer was conditioned by diluting it from stock to 50 uM with PacBio Elution Buffer (catalog no. 100-159-800), then incubating it at 80 C, then cooling it to 4 C. The conditioned primer was annealed to template DNA at 20 C for 30 minutes, then cooled to 4 C for immediate use or to −20 C for storage. Biotinylated template was incubated on ice for 1 hour with 0.1 uM Pol2 polymerase in 80 ul of Flow Comp Flexi beads (Life Tech). 0.1 uM aHL nanopore protein was added to the template polymerase mixture, and allowed to incubate for 40 minutes. The reaction tube was placed on a magnetic separator, and the supernatant was removed and discarded. The beads were washed with 75 mM KGlu, 0.01% Tween20, 20 mM HEPES, 3 mM SrCL2, and 5 mM TCEP. The bead-bound ternary complex was eluted from the beads in 500 mM KGlu, 20 mM HEPES, 2 mM Biotin, 20 mM HEPES, 1 mM SrCL2, 0.0001% Tween20, and 6 mM blocked nucleotides. The supernatant was collected, and the beads were washed again in release buffer to collect residual ternary complex. (W1) and elution fractions (E1 and E2) were visualized by SDS-PAGE (see FIG. 9).

Figure 10:
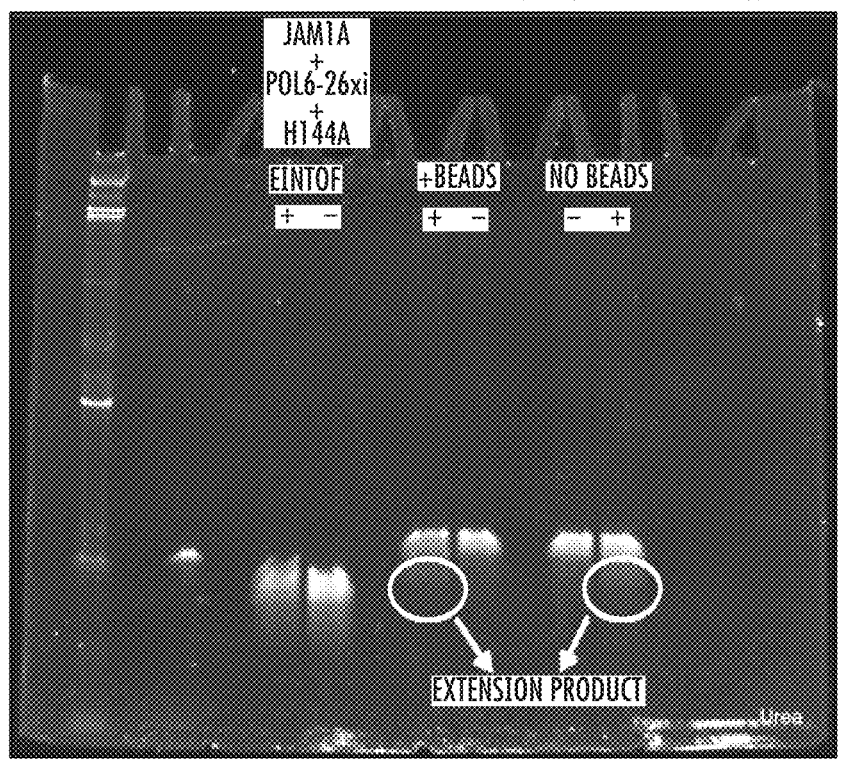
FIG. 10 illustrates a urea gel demonstrating the activity of the polymerase of the complex isolated by the process illustrated in FIG. 8. Reference is made to Example 2.

The polymerase activity of the fraction enriched with ternary complex was assayed for its ability to extend the template in the presence of dNTPs, and the extension product was visualized by urea-SDS-PAGE (see FIG. 10). The polymerase activity obtained by the positive enrichment method was compared polymerase activity of polymerase complexes obtained by a standard method that uses a mixture of template, polymerase, and nanopore to form polymerase complexes (Eintof), but that does not comprise enriching fractions by isolating the polymerase complexes from the unbound components. The results are shown in FIG. 10, which shows that the product of polymerase extension was visible in fractions that had been enriched using the avidin beads according to the positive enrichment. Extension product was not visualized in the mixture resulting from use of the unenriched method (Eintof).

The experiment was repeated using adaptor dimers to provide dumbbell shaped DNA template. A schematic of the process is provided in FIG. 5.

In this instance, an oligonucleotide primer was labeled with desthiobiotin, and incubated with template, polymerase and nanopore. Monomeric streptavidin beads were used for the purification. The enrichment protocol used DNA adaptor dimers as template, Pol2 polymerase, and aHL nanopore in equimolar ratios of 0.1:0.1:0.1. The components were allowed to react for 1.5 hours at 4 C. Two preparations of unenriched mixtures (Eintof) were used as controls. The first unenriched mixture comprised adaptor dimer DNA template, Pol2 polymerase, and aHL in equimolar ratios of 0.4:0.2:0.1; the second unenriched mixture comprised a linear DNA template JAM1A (99 bases), Pol2 polymerase, and aHL nanopore in equimolar ratios of 0.4:0.2:0.1. The components of the unenriched mixtures were incubated overnight at 4 C. The enriched fractions comprising the ternary complexes obtained by the positive enrichment method were applied onto the membrane of a biochip and single pore insertions number of active cells, and sequencing yield were compared to those obtained using polymerase complexes present in the unenriched mixture of the standard Eintof method.

Figure 11:
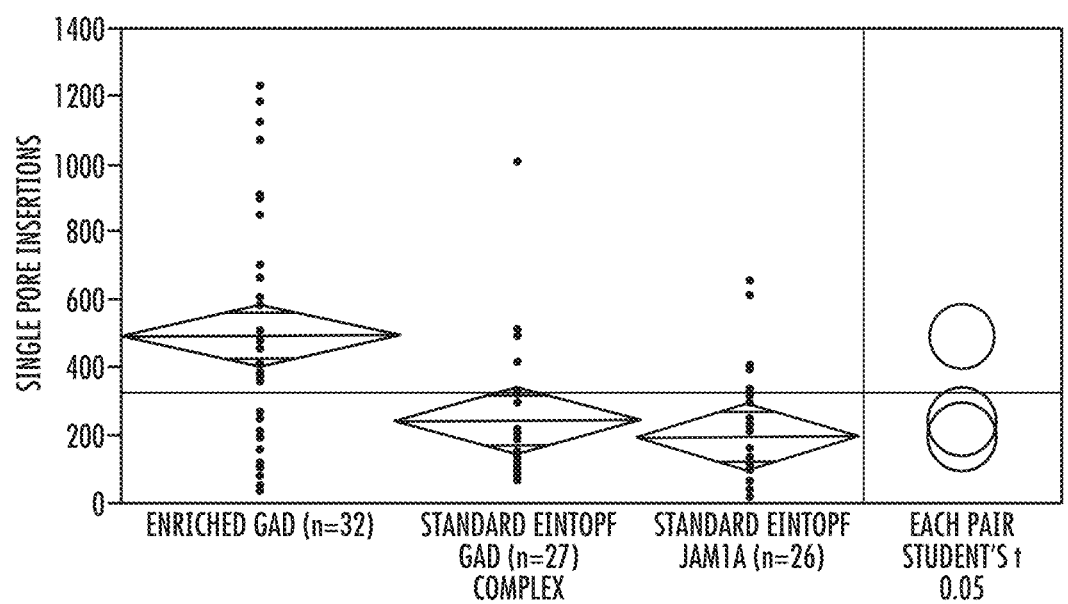
FIG. 11 illustrates the comparison of the number of nanopores inserted in the membrane of a biochip when: (A) the nanopores are comprised in preformed polymerase complexes as shown in FIG. 8; and when (B) and (C) components of the polymerase complex are admixed and allowed to insert into the membrane without prior isolation of a pre-formed polymerase complex. Reference is made to Example 2.

The number of inserted nanopores (single pore insertions) obtained by the positive isolation method, was compared to the number of pore insertions obtained using the standard. Eintof mixture of unenriched fractions when complexed with the GAD template substrate or the JAM1a. The results are shown in FIG. 11 and Table 1A.

Figure 12:
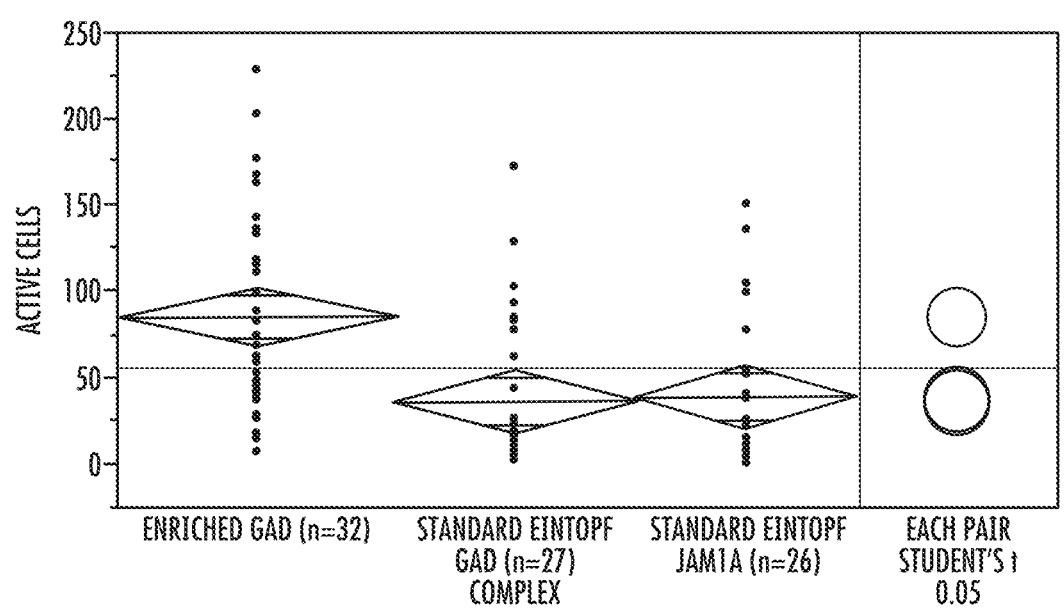
FIG. 12 illustrates the number of active cells that correspond to the nanopores inserted as shown in FIGS. 10 (A), (B), and (C). Reference is made to Example 2.

The number of active cells obtained by the positive isolation method, was compared to the number of pore insertions obtained using the standard. Eintof mixture of unenriched fractions when complexed with the GAD template substrate or the JAM1A. The results are shown in FIG. 12 and Table 1B.

Figure 13:
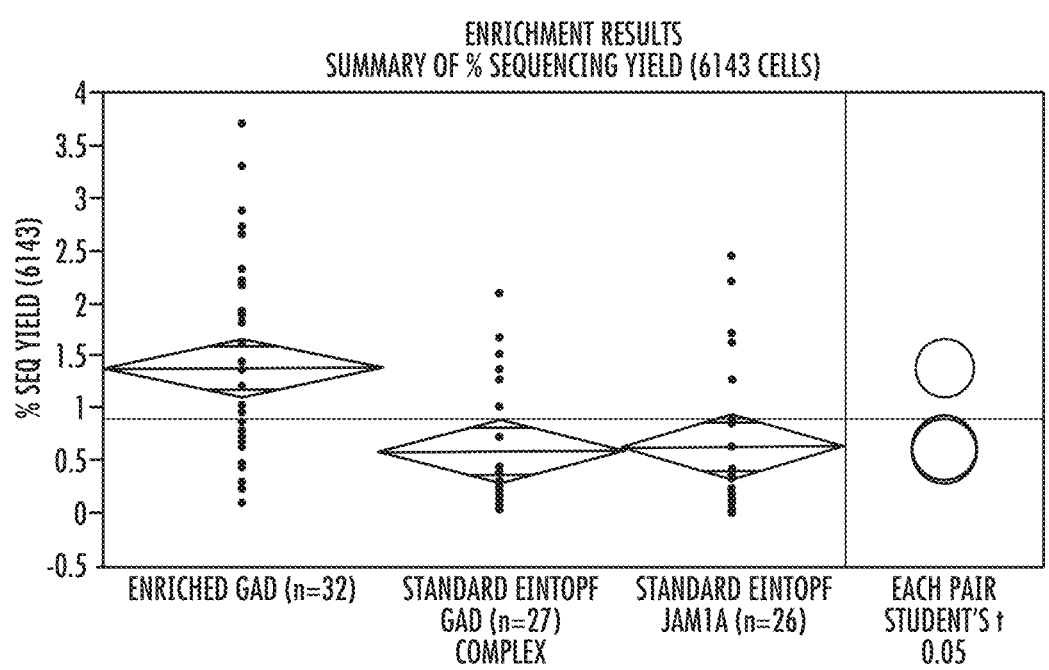
FIG. 13 illustrates the percent sequencing yield obtained for number of active cells that correspond to the nanopores inserted as shown in FIGS. 10 (A), (B), and (C) relative to the total number of cells present on the biochip. Reference is made to Example 2.

The percent sequencing yield measured as a percent of active cells of the total number of cells (6143) present on the, was compared to the percent sequencing yield obtained using the standard. Eintof mixture of unenriched fractions when complexed with the GAD template substrate or the JAM1A. The results are shown in FIG. 13 and Table 1C. The sample comprising the polymerase complexes enriched by the positive isolation method showed an increase of about 2.3 times that obtained using the standard mixture Eintof method.

A summary of the data is provided in Table 2.

Figure 14:
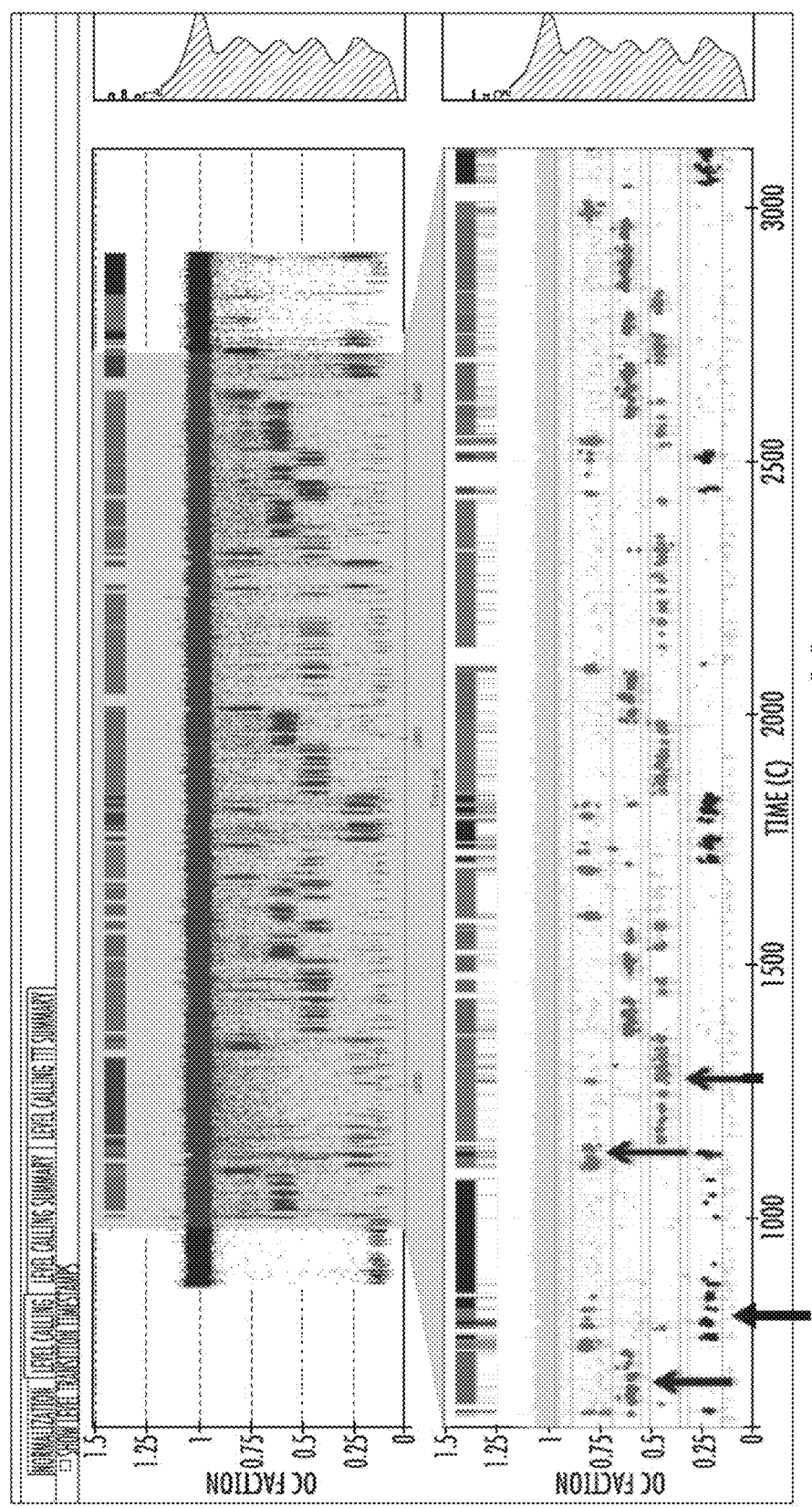
FIG. 14 illustrates an exemplary current trace of nanopore sequencing a polynucleotide template on a biochip comprising polymerase complexes isolated according to the positive isolation method described herein. The four different bases are shown in four different colors as indicated by the arrows.

An example of the current trace obtained using the isolated polymerase complexes is given in FIG. 14. Tags of the tagged nucleotides incorporated into a template dependent DNA strand are shown in green, black, blue and red. The method used for sequencing using tags is described in PCT/US2013/068967 (entitled "Nucleic Acid Sequencing Using Tags" filed on Nov. 7, 2013, which is herein incorporated by reference in its entirety).

The data show that the number of pore insertions, the number of active cells, and the percent sequencing yield obtained using fractions enriched in polymerase complexes obtained by the positive isolation method described herein were at least 100% greater than the same parameters measured for polymerase complexes obtained in mixtures provided by the standard Eintof method.

TABLE 1A

|  | Number | Mean* | Std. Error | Lower 95% | Upper 95% |
|---|---|---|---|---|---|
| Enriched positive isolation method (GAD template) | 32 | 490.000 | 46.46 | 397.56 | 582.44 |
| Standard unenriched Eintof method (GAD template) | 27 | 238.778 | 50.5877 | 138.14 | 339.41 |
| Standard unenriched Eintof method (JAM1A template) | 26 | 190.346 | 51.551 | 87.80 | 292.90 |

*Means for Oneway Anova

TABLE 1B

|  | Number | Mean* | Std. Error | Lower 95% | Upper 95% |
|---|---|---|---|---|---|
| Enriched positive isolation method (GAD template) | 32 | 83.9063 | 8.4863 | 67.024 | 100.79 |
| Standard unenriched Eintof method (GAD template) | 27 | 34.8519 | 9.2387 | 16.473 | 53.23 |
| Standard unenriched Eintof method (JAM1A template) | 26 | 37.5000 | 9.4147 | 18.771 | 56.23 |

*Means for Oneway Anova

TABLE 1C

|  | Number | Mean* | Std. Error | Lower 95% | Upper 95% |
|---|---|---|---|---|---|
| Enriched positive isolation method (GAD template) | 32 | 1.36587 | 013816 | 1.0910 | 1.6407 |
| Standard unenriched Eintof method (GAD template) | 27 | 0.56726 | 0.15041 | 0.2681 | 0.8665 |
| Standard unenriched Eintof method (JAM1A template) | 26 | 0.61038 | 0.15327 | 0.3055 | 0.9153 |

*Means for Oneway Anova

TABLE 2

|  | Enriched positive isolation method (GAD template) | Standard unenriched Eintof method (GAD template) | Standard unenriched Eintof method (JAM1A template) |
|---|---|---|---|
| Total # stations | 32 | 27 | 26 |
| Avg. Single pores | 490 | 239 | 190 |
| Avg. Active cells | 84 | 35 | 38 |
| Avg % Seq Yield (6143 electrodes) | 1.366 | 0.528 | 0.635 |

Example 3

Negative Enrichment—Isolation of polymerase complexes

This example relates to a method for purifying a nanopore sequencing complex, or a polymerase complex, by negatively isolating the desired complexes i.e. nanopore sequencing complex, or a polymerase complex from a mixture of complex components. The complex components are positively isolated by attaching them to a solid phase support, leaving the desired complexes in the unbound fraction.

A schematic of the process is provided in FIG. 7.

CITATION LIST

Patent Literature

PCT/US2013/068967 (published as WO2014/074727 on 15 May 2014; Genia Technologies; entitled. NUCLEIC ACID SEQUENCING USING TAGS).

PCT/US2005/009702 (published as WO2006/028508 on 16 Mar. 2006; President and Fellows of Harvard College; entitled METHODS AND APPARATUS FOR CHARACTERIZING POLYNUCLEOTIDES.

PCT/US2011/065640 (published as WO2012/083249; Columbia University; entitled DNA SEQUENCING BY SYNTHESIS USING MODIFIED NUCLEOTIDES AND NANOPORE DETECTION).

PCT/US2014/061854 (published as WO2015/061511, Genia Technologies, Inc.; entitled PROCESS FOR BIOSENSOR WELL FORMATION).

PCT/US2014/061853 (published as WO2015/061510, Genia Technologies, Inc.; entitled METHODS FOR FORMING LIPID BILAYERS ON BIOCHIPS).

U.S. patent application Ser. No. 14/073,445 (published as US2014/0134616, Genia Technologies, Inc.; entitled NUCLEIC ACID SEQUENCING USING TAGS.

PCT/US2011/065640 (published as WO2012/083249; Columbia University; entitled DNA SEQUENCING BY SYNTHESIS USING MODIFIED NUCLEOTIDES AND NANOPORE DETECTION).

U.S. Pat. No. 6,022,951 entitled STREPTAVIDIN MUTANT'S.
U.S. Pat. No. 6,391,571 entitled RECOMBINANT STREPTAVIDIN MUTANTS.
U.S. Pat. No. 6,312,916 entitled RECOMBINANT STREPTAVIDIN MUTANTS.
U.S. Pat. No. 6,417,331 entitled RECOMBINANT STREPTAVIDIN MUTANTS.
U.S. Pat. No. 6,165,750 entitled MODIFIED AFFINITY STREPTAVIDIN.
U.S. Pat. No. 6,156,493 entitled MODIFIED AFFINITY STREPTAVIDIN.
U.S. Pat. No. 5,168,049 entitled PRODUCTION OF STREPTAVIDIN-LIKE POLYPEPTIDES.
U.S. Pat. No. 4,656,252 entitled. AMIDOBIOTIN COMPOUNDS USEFUL IN A AVIDIN-BIOTIN LAYERING PROCESS.
U.S. Pat. No. 4,478,914 entitled PROCESS FOR APPLYING MULTIPLE LAYERS OF A PROTEIN AND A LIGAND EXTENDER TO A SURFACE AND TO THE MULTIPLE-LAYER SYSTEM.
U.S. Pat. No. 4,282,287 entitled BIOCHEMICAL AVIDIN-BIOTIN MULTIPLE-LAYER SYSTEM.
U.S. Pat. No. 5,215,927 entitled METHOD FOR IMMUNOSELCTION OF CELLS USING AVIDIN AND BIOTIN.

Non-Patent Literature

Astier et al., "Toward single molecule DNA sequencing: direct identification of ribonucleoside and deoxyribonucleoside 5'-monophosphates by using an engineered protein nanopore equipped with a molecular adapter", J Am Chem Soc 128:1705-1710 [2006].
Zakeri et al. "Peptide tag forming a rapid covalent bond to a protein, through engineering a bacterial adhesin", PNAS109:E690-E697 [2012].
Thapa et al., "Native Chemical Ligation": A Boon to Peptide Chemistry", Molecules 19:14461-14483 [2014].
Wu and Guo, "Sortase-Mediated Transpeptidation for Sit-Specific Modification of Peptides, Glycopeptides, and Proteins", J Carbohydr Chem 31:48-66 [2012].
Heck et al., "Enzyme-catalyzed protein crosslinking", Appl Microbiol Biotechnol 97:461-475 [2013].
Dennler et al., "Transglutaminase-Based Chemo-Enzymatic Conjugation Approach Yields Homogenoeous Antibody-Drug Conjugates", Bioconjug Chem 25:569-578 [2014].
Rachidian et al., "Chemoenzymatic Labeling of Proteins: Techniques and Approaches", Bioconjug Chem 24:1277-1294 [2013].
Horhota et al. "Glycerol Nucleoside Triphosphates: Synthesis and Polymerase Substrate Activities", Organic Letters, 8:5345-5347 [2006].
Olejnik et al., "Photocleavable Biotin Phosphoramidite for 5'-end-Labeling, Affinity Purification and Phosphorylation of Synthetic Oligonucleotides" Nucleic Acids Res. 24: 361-366 1996].
Ding et al., "Temperature control of biotin binding and release with a streptavidin-poly(N-isopropylacrylamide) site-specific conjugate", Bioconjugate Chem. 10: 395-400 [1999].
Bulmus et al., "Site-specific polymer-streptavidin bioconjugate for pH-controlled binding and triggered release of biotin", Bioconjugate Chem. 11:78-83 [2000].
Hirsch et al. "Easily reversible desthiobiotin binding to streptavidin, avidin, and other biotin-binding proteins: uses for protein labeling, detection, and isolation", Anal. Biochem. 308, 343-357 [2002].
Piran & Riordan. J. "Dissociation rate constant of the biotin-streptavidin complex", Immunol. Methods 133, 141-143 H9901.
Bayer and Wilchek, "Avidin-biotin technology: preparation of avidin conjugates", Methods in Molec. Biology 10, 143. [1992].

The invention claimed is:

1. A method for isolating active polymerase complexes, said method comprising:

providing a reaction mixture comprising:

(a1) a polymerase complex comprising:

(a1a) a nucleic acid adaptor for isolating active polymerase complexes, said adaptor having a single-stranded region comprising a primer recognition sequence, a runway sequence located 5' to the primer recognition sequence, and a polymerase termination sequence located 5' to the runway sequence, wherein:

said runway sequence comprises a nucleotide sequence having between 2 and 50 contiguous nucleotide bases selected from no more than three of the four nucleotide bases of adenine, cytosine, guanine, and thymine, the nucleotide base that is not contained in the runaway sequence is designated as a stop base, said runway sequence functions as a template for polymerase-driven primer extension, and said polymerase termination sequence comprises at least one stop base that is effective to terminate any such polymerase-driven primer extension;

(a1b) a primer specific to the primer recognition sequence of the adaptor; and (a1c) a polymerase enzyme; and (a2) a nucleic acid sample, wherein the adaptor of the polymerase complex is ligated to said nucleic acid sample;

(b) providing a deoxynucleotide triphosphate (dNTP) mixture comprising only those dNTPs that are complementary to the nucleotide bases contained in the runway sequence of the adaptor, wherein one or more of the dNTPs is modified to include a capture moiety having affinity to a binding partner;

(c) combining the reaction mixture and the dNTP mixture: enable synthesis of a polynucleotide sequence complementary to the runway sequence by the activity of the polymerase to obtain a plurality of active polymerase complexes comprising extended runway complementary sequences having modified dNTPs incorporated therein;

(d) binding said active polymerase complexes to a solid phase support, wherein the capture moieties of the modified dNTPs are bound to binding partners on the solid phase support; and (e) isolating said active polymerase complexes having the extended runway complementary sequences from inactive polymerase complexes comprising unextended runway complementary sequences.

2. The method of claim 1, wherein said isolating comprises washing away the inactive polymerase complexes to yield active polymerase complexes bound to the solid phase support.

3. The method of claim 2, further comprising eluting the active polymerase complexes from the solid phase support.

4. The method of claim 1, wherein said single-stranded region of the adaptor is a linear or a circular template.

5. The method of claim 1, wherein said binding of said active polymerase complex to said solid phase support is reversible.

6. The method of claim 1, wherein said capture moiety is a biotin or modified biotin and said binding partner is streptavidin or modified streptavidin.

7. The method of claim 6, where said biotin compound or said modified biotin compound comprises desthiobiotin or a derivative thereof and said binding partner comprises streptavidin or a derivative thereof.

8. The method of claim 1, wherein the isolated active polymerase complexes each comprise a nanopore.

* * * * *

SEQUENCE LISTING

```
<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: /note="This sequence may encompass 1-3 "GGGGS"
      repeating units wherein some positions may be absent"
<220> FEATURE:
<221> NAME/KEY: MISC_FEATURE
<222> LOCATION: (6)..(15)
<223> OTHER INFORMATION: /note="Variant residues given in the sequence
      have no preference with respect to those in the annotations for
      variant positions"

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 5
<212> TYPE: PRT
<213> ORGANISM: Artificial Sequence
<220> FEATURE:
```

```
<223> OTHER INFORMATION: Synthetic peptide

<400> SEQUENCE: 2

Arg Ser Lys Leu Gly
1               5

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 3
actaccagtt agagtaga                                              18

<210> SEQ ID NO 4
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 4
tctactctaa ct                                                    12

<210> SEQ ID NO 5
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 5
atgtgaccta t                                                     11
```